(12) United States Patent
Taylor et al.

(10) Patent No.: US 7,135,289 B2
(45) Date of Patent: Nov. 14, 2006

(54) METHODS AND COMPOSITIONS FOR MUTATION ANALYSIS OF POLYNUCLEOTIDES BY LIQUID CHROMATOGRAPHY

(75) Inventors: Paul D. Taylor, Gilroy, CA (US); Liem T. Nguyen, San Jose, CA (US)

(73) Assignee: Transgenomic, Inc., Omaha, NE (US)

( * ) Notice: Subject to any disclaimer, the term of this patent is extended or adjusted under 35 U.S.C. 154(b) by 683 days.

(21) Appl. No.: 10/266,906

(22) Filed: Oct. 7, 2002

(65) Prior Publication Data

US 2003/0225261 A1    Dec. 4, 2003

Related U.S. Application Data

(60) Provisional application No. 60/335,478, filed on Nov. 1, 2001, provisional application No. 60/327,613, filed on Oct. 5, 2001.

(51) Int. Cl.
*C12Q 1/68* (2006.01)
*A61K 7/075* (2006.01)
*A01N 57/26* (2006.01)

(52) U.S. Cl. .............................. 435/6; 510/123; 514/77
(58) Field of Classification Search .................... 435/6; 510/123; 514/77
See application file for complete search history.

(56) References Cited

U.S. PATENT DOCUMENTS

| | | | |
|---|---|---|---|
| 5,459,039 A | 10/1995 | Modrich et al. | 435/6 |
| 5,585,236 A | 12/1996 | Bonn et al. | 435/5 |
| 5,698,400 A | 12/1997 | Cotton et al. | 435/6 |
| 5,772,889 A | 6/1998 | Gjerde et al. | 210/635 |
| 5,795,976 A | 8/1998 | Oefner et al. | 536/25.4 |
| 5,972,222 A | 10/1999 | Gjerde et al. | 210/635 |
| 5,986,085 A | 11/1999 | Gjerde et al. | 536/25.41 |
| 5,997,742 A | 12/1999 | Gjerde et al. | 210/635 |
| 6,017,457 A | 1/2000 | Gjerde et al. | 210/635 |
| 6,030,527 A | 2/2000 | Gjerde et al. | 210/198.2 |
| 6,056,877 A | 5/2000 | Gjerde et al. | 210/635 |
| 6,066,258 A | 5/2000 | Gjerde et al. | 210/635 |
| 6,103,112 A | 8/2000 | Sutton et al. | 210/198.2 |
| 6,197,516 B1 | 3/2001 | Altshuler et al. | 435/6 |
| 6,210,885 B1 | 4/2001 | Gjerde et al. | 435/6 |
| 6,265,168 B1 | 7/2001 | Gjerde et al. | 435/6 |
| 6,287,822 B1 | 9/2001 | Gjerde et al. | 435/91.2 |
| 6,287,882 B1 | 9/2001 | Chang et al. | 438/29 |
| 6,372,142 B1 | 4/2002 | Gjerde et al. | 210/635 |

FOREIGN PATENT DOCUMENTS

WO    WO 98/48913    11/1998

(Continued)

OTHER PUBLICATIONS

Andre et al. "Fidelity and Mutational Spectrum of *Pfu* DNA Polymerase on a Human Mitochondrial DNA Sequence", Genome Research 1997 7:843-852.

(Continued)

*Primary Examiner*—Jezia Riley
(74) *Attorney, Agent, or Firm*—Licata & Tyrrell P.C.; Keith A. Johnson

(57) ABSTRACT

Methods, compositions, and kits for separating heteroduplex and homoduplex DNA molecules in a test mixture by temperature-compression denaturing high performance liquid chromatography (tcDHPLC). The method includes use of nitrogen-containing additives in the mobile phase that allow detection of diverse heteroduplex molecules to be performed at the same pre-selected temperature. An example of a preferred additive is betaine. Standard mixtures of DNA fragments, such as mutation standards containing known heteroduplex and homoduplex molecules, can be used to select the concentration of additive and temperature. Compositions and kits including the mobile phase, mutation standards, PCR primers, separation media, and DNA polymerase are also provided.

29 Claims, 7 Drawing Sheets

FOREIGN PATENT DOCUMENTS

| WO | WO 98/48914 | 11/1998 |
|---|---|---|
| WO | WO 98/56797 | 12/1998 |
| WO | WO 98/56798 | 12/1998 |
| WO | WO 99/07899 | 2/1999 |
| WO | WO 00/15778 | 3/2000 |
| WO | WO 01/19485 | 3/2001 |
| WO | WO 01/46687 A2 | 6/2001 |

OTHER PUBLICATIONS

Aksnes et al., "Kinetic Salt Effects and Mechanism in the Hydrolysis of Positively Charged Esters", J. Chem. Soc. London 1959:103-107.

Ames et al., Methods for Detecting Carcinogens and Mutagens with the *Salmonella*/Mammalian-Microsome Mutagenicity Test Mutation Res. 1975 31:347-364.

Blackburn et al., "Estimation of the Dermal Carcinogenic Activity of Petroleum Fractions Using a Modified Ames Assay" Cell Biol. Toxicol. 1984 1:67-80.

Blackburn et al., "Predicting Carcinogenicity of Petroleum Distillation Fractions Using a Modified *Salmonella* Mutagenicity Assay" Cell Biol. Toxicol. 1986 2:63-84.

Cabrera et al., "A new challenge in fast high-performance liquid chromatography separations", Trends Analytical Chem 1998 17:50-53.

Cargill et al., "Characterization of single-nucleotide polymorphisms in coding regions of human genes", Nature Genet 1999 22:231-238.

Cotton, R.G.H., "Slowly but surely towards better scanning for mutations", TIG 1997 13(2):43-46.

Cooper et al. "An estimate of unique DNA sequence heterozygosity int he human genome", Human Genetics 1985 69:201-205.

Eriksson et al., "Separation of DNA Restriction Fragments by Ion-Pair Chromatography", J. Crhomatography 19986 395:265-274.

Goodwin et al., "Studies on the preparation and characterisation of monodisperse polystyrene latices", Colloid & Polymer Sci. 1974 252:464-471.

Guyer et al., "How is the Human Genome Project doing, and what have we learned so far?", Proc. Natl. Acad. Sci. USA 1995 92:10841-10848.

Hayward-Lester et al., "Accurate and Absolute Quantitative Measurement of Gene Expression by Single-tube RT-PCR and HPLC", Genome Research 1995 5:494-499.

Huber et al., "Rapid Analysis of Biopolymers on Modified Non-Porous Polystyrene—Divinylbenzene Particles" Chromatographia 1993 36:653-658.

Huber et al., "High-Resolution Liquid Chromatography of Oligonucleotides on Nonporous Alkylated Styrene-Divinylbenzene Copolymers" Anal. Biochem. 1993 212:351-358.

Isono et al., "Chemical carcinogens as Frameshift Mutagenes-:*Salmonella* DNA Sequence Sensitive to Mutagenesis by Polycyclic Carcinogens", Proc. Natl. Acad. Sci. USA 71(5):1512-1517.

Jinno et al., "Manarity Recognition of Large Polycyclic Aromatic Hydrocarbons by Various Octadecylsilica Stationary Phases in Non-Acqueous Reversed-Phase Liquid Chromatography", Chromatographia 1989 27(7/8):285-291.

Jones et al. "Optimal temperature Selection for Mutation Detection by Denaturing HPLC and Comparison to Single-Stranded Conformation Polymporphism and Heteroduplex Analysis", Clinical Chemistry 1999 45:8 1133-1140.

Karrer et al., "Die Konfiguration des Nicotins. Optisch aktive Hygrinsäure", Helv. Chim. Acta 1925 8:364-367.

King et al. "Trimethylammoniomethanesulfinate and trimethylammoniomethanesulfonate, the Simplest Sulfonic and Sulfonic Acid Betaines. Revision of the Structure of the Trimethylamine Oxide-Sulfur Dioxide Product", J. Phosphorus Sulfur 985 25:11-20.

Kuklin et al., "Detection of Single-Nucleotide Polymorphisms with the WAVE™ DNA Fragment Analysis System", Genet. Test. 1997/98 1(3):201-206.

Landegren et al., "DNA Diagnostics-Molecular Techniques and Automation", Science 1988 242:229-237.

Lerman et al., "Computational Simulation of DNA Melting and Its Application to Denaturing Gradient Gel Electrophoresis", Meth. Enzymol. 1987 155:482-501.

Liu et al., "Denaturing high performance liquid chromatography (DHPLC) used in the detection of germline and somatic mutations", Nucleic Acid Res. 1998 26:1396-1400.

Llyod et al., "A Comparasion of Glycine, Sarcosine, N, N-Dimethylglycine, Glycinebetaine and N-Modified Betaines as Liposome Cryoprotectants", J. Pharm. Pharmacol. 1992 45:507-511.

Nakanishi et al., "Phase Separation in Silica Sol-Gel System Containing Poly(ethylene oxide). 1. Phase Relation and Gel Morphology", Bull, Chem. Soc. Jpn 1994 67:1327-1335.

Nakanishi et al., "Double Pore Silica Gel Monolith Applied to Liquid Chromatography", J. Sol-Gel Sci. Technol. 1997 8:547-552.

O'Donovan et al., "Blind Analysis of Denaturing High-Performance Liquid Chromatography as a Tool for Mutation Detection", Genomics 1998 52:44-49.

Petro et al., "Molded Monolithic Rod of Macroporous Poly(Styrene-co-divinylbenzene) as a Separation Medium for HPLC of Synthetic Polymers: "On-Column" Precipitation-Redissolution Chromatography as an Alternative to Size Exclusion Chromatography of Styrene Oligomers and Polmyers", Anal Chem 1996 68:315-321.

Poole, Colin F. and Salwa K. Poole, Chromatography Today, Elsevier: New York 1991 pp. 313-342.

Putman et al., "Genetic Toxicology", Toxicology Testing Handbook, Jacobson-Kram and Keller eds., Marcel Dekker New York 2000 127-194.

Skopek et al., Analysis of sequence alterations in a defined DNA region:comparison of temperature-modulated heteroduplex analysis and denaturing gradient gel electrophoresis, Mutat. Res. 1999 430:13-21.

Snyder R.L. and JJ Kirkland, Introduction to Modern Liquid Chromatography 2nd ed. John Wiley & Sons, Inc.,: New York 1979 pp. 272-278.

Underhill et al., "Detection of Numerous Y Chromosome Biallelic Polymorphisms by Denaturing High-Performance Liquid Chromatography", Genome Research 1997 7:996-1005.

Underhill et al., "A pre-Columbian Y chromosome-specific transition and its implications for human evolutionary history", Proc. Natl. Acad. Sci. USA 1996 93:196-200.

Wagner et al., "Denaturing High-Performance Liquid Chromatography Detects Reliably BRCA1 and BRCA2 Mutations", Genomics 1999 62:369-376.

Xiao and Oefner, "Denaturing High-Performance Liquid Chromatography: A Review", Human Mutation 2001 17:439-474.

SEQUENCE LISTING

<160> NUMBER OF SEQ ID NOS: 3

<210> SEQ ID NO 1
<211> LENGTH: 209
<212> TYPE: DNA
<213> ORGANISM: Homo sapiens

<400> SEQUENCE: 1

```
aggcactggt cagaatgaag tgaatggcac acaggacaag tccagaccca ggaaggtcca      60
gtaacatggg agaagaacgg aaggagttct aaaattcagg gctcccttgg gctcccctgt     120
ttaaaaatgt aggttttatt attatatttc attgttaaca aaagtccatg agatctgtgg     180
aggataaagg gggagctgta ttttccatt                                        209
```

<210> SEQ ID NO 2
<211> LENGTH: 219
<212> TYPE: DNA
<213> ORGANISM: Homo sapiens

<400> SEQUENCE: 2

```
ttccctgggt ggccgccgag acgctggccc gggctggagg gatggcgggg cggggacggg      60
ggcggggggcg gggctcgtca cgtggagagg cgcgcggggg cgggcggggc ggggggcgcgc    120
gcccggctcc ttaaaggcgc gcgagccgag cggcgaggtg cctctgtggc cgcaggcgca     180
ggcccgggcg acagccgaga cgtggagcgc gccggctcg                            219
```

<210> SEQ ID NO 3
<211> LENGTH: 338
<212> TYPE: DNA
<213> ORGANISM: Homo sapiens

<400> SEQUENCE: 3

```
taatacgact cactataggg cgaattgggc ccgacgtcgc atgctcccgg ccgccatggc      60
cgcgggattt cacttctagt gcaccattat gacgttacta aaggcagatg cagacttacg     120
ttgcttcaac cactaccccg actccagcag gccgcaaggc ttccgtgatt gctacagcaa     180
tttgttttgt aaggtgctcc tgaactgtgg atgtgataag gagctcagtt tgagagtctg     240
acacaatcac tagtgcggcc gcctgcaggt cgaccatatg ggagagctcc caacgcgttg     300
gatgcatagc ttgagtattc tatagtgtca cctaaata                             338
```

METHODS AND COMPOSITIONS FOR MUTATION ANALYSIS OF POLYNUCLEOTIDES BY LIQUID CHROMATOGRAPHY

CROSS-REFERENCE TO RELATED PATENT APPLICATIONS

This application is a regular U.S. patent application under 35 U.S.C. §111 (a) and 37 U.S.C. §1.53(b) and claims priority from the following co-pending, commonly assigned provisional applications, each filed under 35 U.S.C. §111 (b): U.S. Patent Application Ser. No. 60/327,613, filed Oct. 5, 2001 and Ser. No. 60/335,478, filed Nov. 1, 2001.

FIELD OF THE INVENTION

The present invention concerns improved methods for detection of mutations in nucleic acids. More specifically, the invention concerns methods, compositions, and kits for mutation analysis using temperature-compression denaturing high performance liquid chromatography (tcDHPLC).

BACKGROUND OF THE INVENTION

The ability to detect mutations in double stranded polynucleotides, and especially in DNA fragments, is of great importance in medicine, as well as in the physical and social sciences. The Human Genome Project is providing an enormous amount of genetic information which is setting new criteria for evaluating the links between mutations and human disorders (Guyer et al., Proc. Natl. Acad. Sci. U.S.A 92:10841 (1995)). The ultimate source of disease, for example, is described by genetic code that differs from wild type (Cotton, TIG 13:43 (1997)). Understanding the genetic basis of disease can be the starting point for a cure. Similarly, determination of differences in genetic code can provide powerful and perhaps definitive insights into the study of evolution and populations (Cooper, et. al., Human Genetics vol. 69:201 (1985)).

Understanding these and other issues related to genetic coding is based on the ability to identify anomalies, i.e., mutations, in a DNA fragment relative to the wild type. A need exists, therefore, for a methodology to detect mutations in an accurate, reproducible and reliable manner.

DNA molecules are polymers comprising sub-units called deoxynucleotides. The four deoxynucleotides found in DNA comprise a common cyclic sugar, deoxyribose, which is covalently bonded to any of the four bases, adenine (a purine), guanine (a purine), cytosine (a pyrimidine), and thymine (a pyrimidine), hereinbelow referred to as A, G, C, and T respectively. A phosphate group links a 3'-hydroxyl of one deoxynucleotide with the 5'-hydroxyl of another deoxynucleotide to form a polymeric chain. In double stranded DNA, two strands are held together in a helical structure by hydrogen bonds between, what are called, complementary bases. The complementarity of bases is determined by their chemical structures. In double stranded DNA, each A pairs with a T and each G pairs with a C, i.e., a purine pairs with a pyrimidine. Ideally, DNA is replicated in exact copies by DNA polymerases during cell division in the human body or in other living organisms.

Sometimes, exact replication fails and an incorrect base pairing occurs, which after further replication of the new strand results in double stranded DNA offspring containing a heritable difference in the base sequence from that of the parent. Such heritable changes in base pair sequence are called mutations.

In the present invention, double stranded DNA is referred to as a duplex. When the base sequence of one strand is entirely complementary to base sequence of the other strand, the duplex is called a homoduplex. When a duplex contains at least one base pair which is not complementary, the duplex is called a heteroduplex. A heteroduplex can be formed during DNA replication when an error is made by a DNA polymerase enzyme and a non-complementary base is added to a polynucleotide chain being replicated. A heteroduplex can also be formed during repair of a DNA lesion. Further replications of a heteroduplex will, ideally, produce homoduplexes which are heterozygous, i.e., these homoduplexes will have an altered sequence compared to the original parent DNA strand. When the parent DNA has the sequence which predominates in a natural population it is generally called the "wild type."

Many different types of DNA mutations are known. Examples of DNA mutations include, but are not limited to, "point mutation" or "single base pair mutations" wherein an incorrect base pairing occurs. The most common point mutations comprise "transitions" wherein one purine or pyrimidine base is replaced for another and "transversions" wherein a purine is substituted for a pyrimidine (and visa versa). Point mutations also comprise mutations wherein a base is added or deleted from a DNA chain. Such "insertions" or "deletions" are also known as "frameshift mutations". Although they occur with less frequency than point mutations, larger mutations affecting multiple base pairs can also occur and may be important. A more detailed discussion of mutations can be found in U.S. Pat. No. 5,459,039 to Modrich (1995), and U.S. Pat. No. 5,698,400 to Cotton (1997). These references and the references contained therein are incorporated in their entireties herein.

The sequence of base pairs in DNA codes for the production of proteins. In particular, a DNA sequence in the exon portion of a DNA chain codes for a corresponding amino acid sequence in a protein. Therefore, a mutation in a DNA sequence may result in an alteration in the amino acid sequence of a protein. Such an alteration in the amino acid sequence may be completely benign or may inactivate a protein or alter its function to be life threatening or fatal. Intronic mutations at splice sites may also be causative of disease (e.g. β-thalassemia). Mutation detection in an intron section may be important by causing altered splicing of mRNA transcribed from the DNA, and may be useful, for example, in a forensic investigation.

Detection of mutations is, therefore, of great interest and importance in diagnosing diseases, understanding the origins of disease and the development of potential treatments. Detection of mutations and identification of similarities or differences in DNA samples is also of critical importance in increasing the world food supply by developing diseases resistant and/or higher yielding crop strains, in forensic science, in the study of evolution and populations, and in scientific research in general (Guyer et al., Proc. Natl. Acad. Sci. U.S.A 92:10841 (1995); Cotton, TIG 13:43 (1997)). These references and the references contained therein are incorporated in their entireties herein.

Analysis of DNA samples has historically been done using gel electrophoresis. Capillary electrophoresis has been used to separate and analyze mixtures of DNA. However, these methods cannot distinguish point mutations from homoduplexes having the same base pair length.

Recently, a chromatographic method called ion-pair reverse-phase high pressure liquid chromatography (IP-RP-HPLC), also referred to as Matched Ion Polynucleotide Chromatography (MIPC), was introduced to effectively separate mixtures of double stranded polynucleotides, in general and DNA, in particular, wherein the separations are based on base pair length (Huber, et al., Chromatographia 37:653 (1993); Huber, et al., Anal. Biochem. 212:351 (1993); U.S. Pat. Nos. 5,585,236; 5,772,889; 5,972,222; 5,986,085; 5,997,742; 6,017,457; 6,030,527; 6,056,877; 6,066,258; 6,210,885; and U.S. patent application Ser. No. 09/129,105 filed Aug. 4, 1998.

As the use and understanding of IP-RP-HPLC developed it became apparent that when IP-RP-HPLC analyses were carried out at a partially denaturing temperature, i.e., a temperature sufficient to denature a heteroduplex at the site of base pair mismatch, homoduplexes could be separated from heteroduplexes having the same base pair length (Hayward-Lester, et al., Genome Research 5:494 (1995); Underhill, et al., Proc. Natl. Acad. Sci. U.S.A 93:193 (1996); Doris, et al., DHPLC Workshop, Stanford University, (1997)). Thus, the use of denaturing high performance liquid chromatography (DHPLC) was applied to mutation detection (Underhill, et al., Genome Research 7:996 (1997); Liu, et al., Nucleic Acid Res., 26;1396 (1998)). These chromatographic methods are generally used to detect whether or not a mutation exists in a test DNA fragment.

DHPLC, as known in the art, provides a method for separating heteroduplex and homoduplex nucleic acid molecules (e.g., DNA or RNA) in a mixture using high performance liquid chromatography. In the separation method, a mixture containing both heteroduplex and homoduplex nucleic acid molecules is applied to a stationary reverse-phase support. The sample mixture is then eluted with a mobile phase containing an ion-pairing reagent and an organic solvent. Sample elution is carried out under conditions effective to at least partially denature the heteroduplexes and results in the separation, or at least partial separation, of the heteroduplex and homoduplex molecules.

Single nucleotide polymorphisms (SNPs) are thought to be ideally suited as genetic markers for establishing genetic linkage and as indicators of genetic diseases (Landegre et al. Science 242:229–237 (1988)). In some cases a single SNP is responsible for a genetic disease. According to estimates the human genome may contain over 3 million SNPs. Due to their propensity they lend themselves to very high resolution genotyping. The SNP consortium, a joint effort of 10 major pharmaceutical companies, has announced the development of 300,000 SNP markers and their placement in the public domain by mid 2001.

The efficiency of DHPLC for detection of novel mutations (frequently termed scanning) has been quantified by several authors. Results ranged from 87% detection when a single-temperature analysis was used without any amplicon design (Cargill, et al. Nature Genet. 22:231–238 (1999)) to 100% detection in a blinded study of many polymorphisms within a single, well-behaved amplicon (O'Donovan et al., Genomics 52:44–49 (1998)). Comparisons with single-strand conformation polymorphism (SSCP) (Choy et al., Ann. Hum. Genet. 63:383–391 (1999); Gross et al., Hum. Genet. 105: 72–78 (1999); Dobson-Stone et al., Eur. J. Hum. Genet. 8:24–32. (2000)) and denaturing gradient gel electrophoresis (DGGE) (Skopek et al., Mutat. Res. 430:13–21 (1999)) have shown DHPLC to have a superior detection rate, whereas most recently DHPLC has been shown to detect mutations reliably in BRCA1 and BRCA2 (Wagner et al., Genomics 62:369–376 (1999)).

The ability of DHPLC to detect mutations may be less than 100% in some cases, for example if a mutation site is within a region having high GC content. There is a need for methods, compositions, and devices for improving the ability of DHPLC to detect such mutations.

In DHPLC, the required analysis temperature depends on the sequence of the fragment and on the position of the mutation. DHPLC analysis is typically run at an elevated column temperature (e.g. in the range of about 50° C. to about 80° C.) with the temperature being thermostatically controlled. As described in the prior art (U.S. Pat. Nos. 6,287,882 and 6,103,112), it is preferred to maintain the temperature control within a range of +0.1° C. in order to reliably detect heteroduplexes. However, this requirement increases the cost and complexity of the column temperature control system. For multiple different DNA samples, the column oven must be adjusted for each sample, thus potentially slowing down sample throughput.

Algorithms and software for predicting the temperature for conducting DHPLC have been described (U.S. Pat. Nos. 5,795,976; 6,197,516; 6,287,882; and U.S. patent application Ser. No. 09/469,551 filed Dec. 22, 1999) and are available commercially (Wavemaker® software and Navigator™ software (Transgenomic)) and on the World Wide Web (http://insertion.stanford.edu/melt.html). These programs require that the user input the sequence of the DNA being analyzed. Additional empirical analyses often must be performed, below and above the predicted temperature value, in order to arrive at a suitable temperature for detecting heteroduplexes.

There is a need for DHPLC methods, compositions and systems that minimize the requirement for costly column temperature control devices. There is a need for eliminating the requirement for using a separate column temperature for each fragment being analyzed. There is a need for methods and compositions that can avoid the use of costly software for temperature prediction, and that can avoid the need for conducting multiple empirical analyses.

SUMMARY OF THE INVENTION

In one aspect, the invention concerns a chromatographic method for separating heteroduplex and homoduplex DNA molecules in a test mixture. In one embodiment, the method includes: (a) applying the test mixture to a reverse phase separation medium; (b) eluting the medium of step (a) with a mobile phase comprising at least one nitrogen-containing mobile phase additive, wherein the eluting is carried out under conditions effective to at least partially denature the heteroduplexes and wherein the eluting results in the separation, or at least partial separation, of the heteroduplexes from the homoduplexes. The eluting is preferably carried out at a pre-selected concentration of the additive and at a pre-selected temperature. Examples of a preferred nitrogen-containing additive include betaine, tetramethylammonium chloride, tetraethylammonium chloride, triethylamine hydrochloride, and choline. A preferred mobile phase includes an organic solvent and an ion pairing agent, and can include a chelating agent such as EDTA. The mobile phase preferably possess a pH in the range of 4 to 9, and is preferably aqueous. The elution is preferably performed at a temperature of less than about 50° C. The additive is preferably present at a concentration at which first heteroduplex molecules from a first mixture can be observed at the pre-selected temperature, and wherein second heteroduplex molecules from a second mixture can be observed at the pre-selected temperature. Examples of the first mixture and second mixture are mutation standards containing known nucleic acid molecules and which form previously characterized heteroduplexes and homoduplexes upon hybridization. For example, the first mixture can include a hybridization product of the double stranded sequence variant 168A and sequence variant 168G, wherein the 168A variant corresponds to the nucleic acid identified by SEQ ID NO: 1 (DYS271); and the second mixture can include a hybridization product of the double stranded sequence variant 46C and sequence variant 46G, wherein the 46C variant corresponds to the nucleic acid identified by SEQ ID NO: 2 (HTM219).

A preferred additive is betaine which can be present at a mobile phase concentration of about 0.5 to about 6 M, preferably at a concentration in the range of about 2 to about 5 M; and more preferably at a concentration of about 4 M. The temperature of the mobile phase is preferably in the range of about 25° C. to 80° C., and preferably less than about 50° C. The betaine has preferably been treated with at least one of activated charcoal and ion-exchange resin. A preferred ion-exchange resin is chelex-100. An example of a suitable counterion agent is triethylammonium acetate (TEAA).

Non-limiting examples of nitrogen-containing additives useful in tcDHPLC include a compound according to the formula:

(I)

wherein:
$R^1$, $R^2$, and $R^3$, may be the same or different and are independently selected from the group consisting of hydrogen, methyl, ethyl, hydroxyethyl, and propyl, with the proviso that no more than two of $R^1$, $R^2$, and $R^3$ are hydrogen; and X is a moiety selected from the group consisting of:

radicals of the formulas

=O;

→O

—$CH_3$;

—$CH_2CH_3$; and

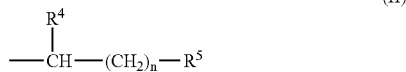

(II)

wherein:
$R^4$ is selected from the group consisting of methyl and hydrogen and, when combined with $R^1$, forms a pyrrolidine ring;
$R^5$ is selected from the group consisting of —$CO_2H$, —$CH_2OH$, and —$SO_3H$; and
n is an integer of from 0 to 2;
with the proviso that, when $R^1$ and $R^4$ form a pyrrolidine ring, no more than one of $R^2$ and $R^3$ is hydrogen. In one embodiment, $R^1$, $R^2$ and $R^3$ can be the same or different and selected from the group consisting of methyl, ethyl and hydrogen with the proviso that no more than two of $R^1$, $R^2$ and $R^3$ are hydrogen and, when $R^1$ and $R^4$ form a pyrrolidine ring, no more than one of $R^2$ and $R^3$ is hydrogen. In another embodiment, X is —$CH_2CO_2H$. In still another embodiment, X is —$CH_2CO_2H$ and $R^1$, $R^2$, and $R^3$ are methyl. In another embodiment, $R^1$, $R^2$ and $R^3$ are methyl. $R^1$ and $R^2$ can be methyl and $R^3$ is hydrogen. $R^1$ can be methyl and $R^2$ and $R^3$ are hydrogen. In a further embodiment, X is =O. In other embodiments: $R^1$, $R^2$ and $R^3$ are methyl; $R^1$ and $R^4$ form a pyrrolidine ring, $R^2$ and $R^3$ methyl, n is 0, and $R^5$ is —$CO_2H$; and $R^1$, $R^2$ and $R^3$ are methyl and X is —$CH_2SO_3$.

In another aspect, the invention concerns a composition including an aqueous mobile phase maintained at a preselected temperature during analysis of double-stranded nucleic acids by temperature-compression denaturing high performance liquid chromatography. The mobile phase preferably includes a nitrogen containing additive as described herein. The mobile phase preferably further includes a counterion agent and an organic solvent, and can include a chelating agent such ad EDTA. An example of a preferred additive is betaine which can be present at a concentration in the range of about 2 to about 5 M and preferably at a concentration of about 4 M. The composition can include a reverse phase separation medium maintained at the preselected temperature. Examples of a suitable medium include polymeric beads, silica particles or monolithic separation columns. The medium can be contained in a capillary device. During the analysis, the mobile phase is preferably maintained at a temperature less than about 50° C., and more preferably in the range of about 30° C. to about 49° C. The mobile phase is capable of eluting double stranded DNA from a reverse phase separation medium, and preferably includes ion-pairing reagent and organic solvent.

In yet another aspect, the invention concerns one or more kits for use in temperature-compression denaturing high performance liquid chromatography. The kit can include one or more of: a mutation standard: double-stranded DNA corresponding with the nucleic acid identified by SEQ ID NO: 1; double-stranded DNA corresponding with the nucleic acid identified by SEQ ID NO: 2; a reverse-phase separation column; a proof-reading DNA polymerase such as Pho or Taq polymerase; in a separate container, mobile phase including a nitrogen-containing additive as described herein.

In still another aspect, the invention concerns a chromatographic method for separating heteroduplex and homoduplex DNA molecules in a test mixture. In an preferred embodiment, the method includes: (a) applying the test mixture to a reverse phase separation medium, (b) eluting the medium of step (a) with a mobile phase comprising a nitrogen-containing additive of the invention (e.g. at least one of betaine, tetramethylammonium chloride, tetraethylammonium chloride, triethylamine hydrochloride, and choline). The eluting is carried out under conditions effective to at least partially denature the heteroduplexes and wherein the eluting results in the separation, or at least partial separation, of the heteroduplexes from the homoduplexes. The eluting is effected at a pre-selected concentration of additive and at a pre-selected temperature. The additive is preferably present at a concentration at which first heteroduplex molecules from a first mixture and second heteroduplex molecules from a second mixture can be observed at the pre-selected temperature. The first heteroduplex molecules have different value of T(hsst) than the second heteroduplex molecules. Examples of such first and second mixtures include mutation standards. Example of suitable standards include DYS271 and HTM219 as described herein. In one embodiment, the additive is betaine present in the range of about 3M to about 5M and the temperature is less than about 50° C. In another embodiment, the betaine is present at a concentration of 4M and the temperature is 43° C. The separation medium can include polymeric or silica based beads.

In another aspect, the invention concerns a method for selecting a concentration of nitrogen-containing additive, such as betaine, to be used in mobile phase during temperature-compression denaturing high performance liquid chromatography. The method includes: (a) applying a first mixture comprising first heteroduplex molecules and first homoduplex molecules to a reverse phase separation medium, (b) eluting the medium of step (a) with a mobile phase comprising the additive, wherein said eluting is carried out under conditions effective to at least partially denature said first heteroduplexes and wherein the eluting results in separation of said first heteroduplexes from said first homoduplexes, wherein said eluting in step (a) is effected at a pre-selected temperature, (c) applying a second mixture comprising second heteroduplex molecules and second homoduplex molecules to said reverse phase separation medium, (d) eluting the medium of step (c) with a mobile phase comprising the additive, wherein said eluting is carried out under conditions effective to at least partially denature said second heteroduplexes and wherein the eluting results in separation of said second heteroduplexes from said second homoduplexes, wherein said eluting is effected at said pre-selected temperature, (e) selecting an additive concentration in the range of about 2M to about 5M at which said first heteroduplexes can be detected in step (c) and wherein said second heteroduplexes can be detected in step (d), wherein said first mixture comprises a hybridization product of the double stranded sequence variant 168A and sequence variant 168G, wherein the 168A variant corresponds to the nucleic acid identified by SEQ ID NO: 1, wherein said second mixture comprises a hybridization product of the double stranded sequence variant 46C and sequence variant 46G, wherein the 46C variant corresponds to the nucleic acid identified by SEQ ID NO: 2.

In another aspect, the invention concerns a chromatographic method for separating heteroduplex and homoduplex DNA molecules in a mixture. One embodiment of the method includes: applying the mixture to a stationary reverse phase support, eluting the heteroduplex and homoduplex molecules of the mixture with a mobile phase containing an ion-pairing reagent and an organic solvent, wherein the eluting is carried out under conditions effective to at least partially denature said heteroduplexes and where the eluting results in the separation of said heteroduplexes from said homoduplexes, wherein the eluting is carried out at a pre-selected temperature of less than 50° C., and wherein the mobile phase includes a nitrogen-containing additive selected from the group consisting of betaine, tetramethylammonium chloride, tetraethylammonium chloride, triethylamine hydrochloride, choline, and mixtures thereof. A preferred additive is betaine. The method can be carried out at a temperature less than 50° C. and preferably in a range of about 25° C. to about 49° C. The stationary support can be composed of an alkylated base material. Examples of a suitable said base material include silica, alumina, zirconia, polystyrene, polyacrylamide, and styrene-divinyl copolymers.

In a still further aspect, the invention provides a chromatographic method for separating heteroduplex and homoduplex DNA molecules in a mixture. An embodiment of the method includes: applying the mixture to a stationary reverse phase support, eluting the heteroduplex and homoduplex molecules of the mixture with a mobile phase containing an ion-pairing reagent and an organic solvent, wherein the eluting is carried out under conditions effective to at least partially denature the heteroduplexes and where the eluting results in the separation of the heteroduplexes from the homoduplexes, wherein the eluting is carried out at a pre-selected temperature of less than 50° C., and wherein the mobile phase includes betaine. The betaine can be present in the range of about 2 to about 5 M. The stationary support can be composed of an alkylated base material. Examples of a suitable said base material include silica, alumina, zirconia, polystyrene, polyacrylamide, and styrene-divinyl copolymers.

DETAILED DESCRIPTION OF THE INVENTION

Figure 1:
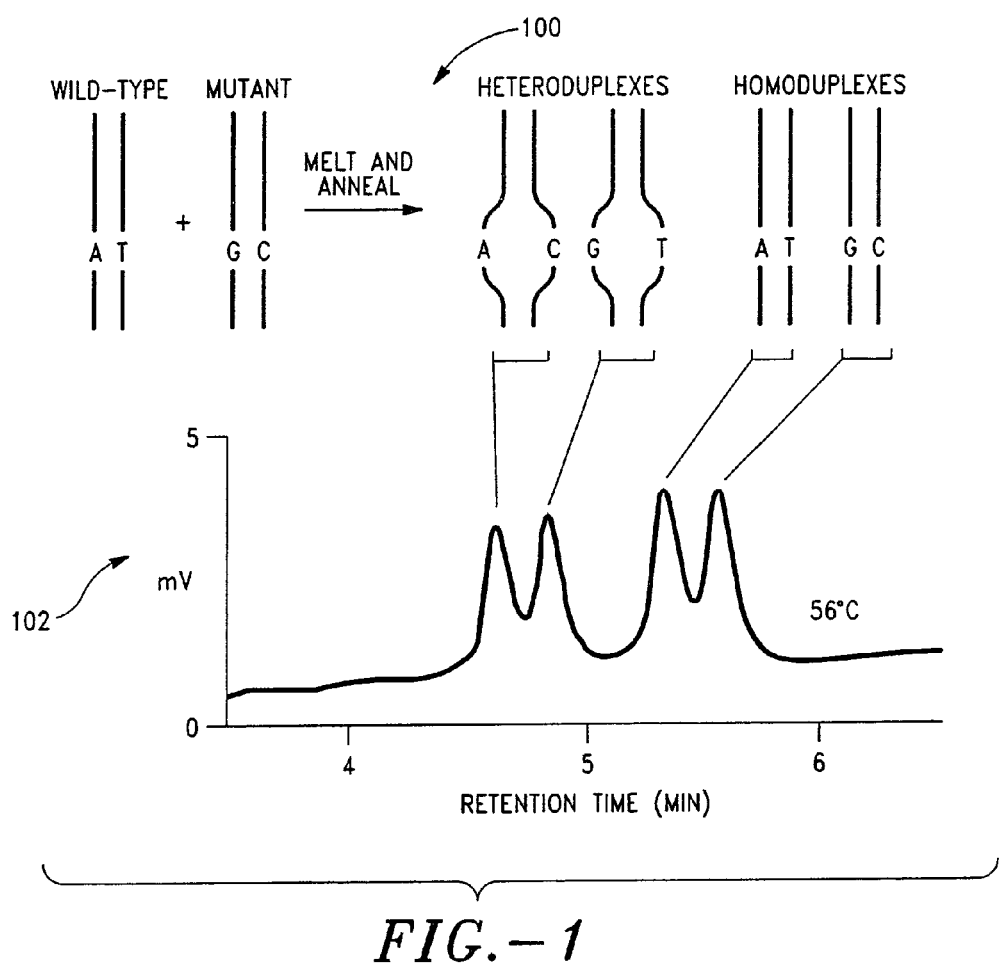
FIG. 1 shows a schematic representation of a hybridization to form homoduplex and heteroduplex molecules.

A reliable way to detect mutations is by hybridization of the putative mutant strand in a sample with the wild type strand (Lerman, et al., Meth. Enzymol. 155:482 (1987)). If a mutant strand is present, then, typically, two homoduplexes and two heteroduplexes will be formed as a result of the hybridization process. Hence separation of heteroduplexes from homoduplexes provides a direct method of confirming the presence or absence of mutant DNA segments in a sample.

In a general aspect, the instant invention concerns chromatographic separation of DNA fragments for analysis of mutations in DNA. Recently, a chromatographic method called ion-pair reverse-phase high performance liquid chromatography (IP-RP-HPLC), also referred to as Matched Ion Polynucleotide Chromatography (MIPC), was introduced to effectively separate mixtures of double stranded polynucleotides, in general and DNA, in particular, wherein the separations are based on base pair length (Huber, et al., Chromatographia 37:653 (1993); Huber, et al., Anal. Biochem. 212:351 (1993); U.S. Pat. Nos. 5,585,236; 5,772,889;

5,972,222; 5,986,085; 5,997,742; 6,017,457; 6,030,527; 6,056,877; 6,066,258; 6,210,885; and U.S. patent application Ser. No. 09/129,105 filed Aug. 4, 1998.

"Reversed phase support" refers to a stationary support (including the base material and any chemically bonded phase) for use in liquid chromatography, particularly high performance liquid chromatography (HPLC), which is less polar (e.g., more hydrophobic) than the starting mobile phase.

"Ion-pair (IP) chromatography" refers to a chromatographic method for separating samples in which some or all of the sample components contain functional groups which are ionized or are ionizable. Ion-pair chromatography is typically carried out with a reversed phase column in the presence of an ion-pairing reagent.

"Ion-pairing reagent" is a reagent which interacts with ionized or ionizable groups in a sample to improve resolution in a chromatographic separation. An "ion-pairing agent" refers to both the reagent and aqueous solutions thereof. An ion-pairing agent is typically added to the mobile phase in reversed phase liquid chromatography for optimal separation. The concentration and hydrophobicity of an ion-pairing agent of choice will depend upon the number and types (e.g., cationic or anionic) of charged sites in the sample to be separated.

"Primer" refers to an oligonuleotide, whether occurring naturally as in a purified restriction digest or produced synthetically, which is capable of acting as a point of initiation of synthesis when placed under conditions in which synthesis of a primer extension product that is complementary to a target nucleic acid strand is induced, i.e., in the presence of nucleotides and an agent for polymerization (such as a DNA polymerase) and at a suitable temperature and pH. The primer is preferably single stranded for maximum efficiency in amplification. Preferably, the primer is an oligodeoxyribonucleotide. The primer must be sufficiently long to prime the synthesis of extension products (referred to herein as "PCR products" and "PCR amplicons") in the presence of the polymerization agent.

Alterations in a DNA sequence which are benign or have no negative consequences are sometimes called "polymorphisms". In the present invention, any alterations in the DNA sequence, whether they have negative consequences or not, are called "mutations". It is to be understood that the method of this invention has the capability to detect mutations regardless of biological effect or lack thereof. For the sake of simplicity, the term "mutation" will be used throughout to mean an alteration in the base sequence of a DNA strand compared to a reference strand. It is to be understood that in the context of this invention, the term "mutation" includes the term "polymorphism" or any other similar or equivalent term of art.

A "homoduplex" is defined herein to include a double stranded DNA fragment wherein the bases in each strand are complementary relative to their counterpart bases in the other strand. "Homoduplex molecules" are typically composed of two complementary nucleic acid strands.

A "heteroduplex" is defined herein to include a double stranded DNA fragment wherein at least one base in each strand is not complementary to at least one counterpart base in the other strand. "Heteroduplex molecules" are typically composed of two complementary nucleic acid strands (e.g., DNA), where the strands have less than 100% sequence complementarity. Since at least one base pair in a heteroduplex is not complementary, it takes less energy to separate the bases at that site compared to its fully complementary base pair analog in a homoduplex. This results in the lower melting temperature at the site of a mismatched base of a heteroduplex compared to a homoduplex. A heteroduplex can be formed by annealing of two nearly complementary sequences. A heteroduplex molecule that is "partially denatured" under a given set of chromatographic conditions refers to a molecule in which several complementary base pairs of the duplex are not hydrogen-bond paired, such denaturing typically extending beyond the site of the base-pair mismatch contained in the heteroduplex, thereby enabling the heteroduplex to be distinguishable from a homoduplex molecule of essentially the same size. In accordance with the present invention, such denaturing conditions may be either chemically (e.g., resulting from pH conditions) or temperature-induced, or may be the result of both chemical and temperature factors.

The term "heteromutant" includes a DNA fragment containing non-complementary base pair.

The "heteromutant site separation temperature" T(hsst) includes the temperature which preferentially denatures the heteroduplex DNA at a site of mutation and which gives the greatest difference in the degree of denaturation between the heteroduplexes and homoduplexes. This is a temperature which is optimal to effect a chromatographic separation of heteroduplexes and homoduplexes by DHPLC and hence, detect mutations.

The term "hybridization" refers to a process of heating and cooling a double stranded DNA (dsDNA) sample, e.g., heating to 95° C. followed by slow cooling. The heating process causes the DNA strands to denature. Upon cooling, the strands re-combine, or re-anneal, into duplexes.

When mixtures of DNA fragments are mixed with an ion pairing agent and applied to a reverse phase separation column, they are separated by size, the smaller fragments eluting from the column first. However, when IP-RP-HPLC is performed at an elevated temperature which is sufficient to denature that portion of a DNA fragment domain which contains a site of mismatch, then heteroduplexes separate from homoduplexes. IP-RP-HPLC, when performed at a temperature which is sufficient to partially denature a heteroduplex, is referred to as DHPLC. DHPLC is also referred to in the art as "Denaturing Matched Ion Polynucleotide Chromatography" (DMIPC).

In a typical experiment, a test nucleic acid fragment is hybridized with a wild type fragment and analyzed by DHPLC. If the test fragment contains a mutation, then the hybridization product ideally includes both homoduplex and heteroduplex molecules. If no mutation is present, then the hybridization only produces homoduplex wild type molecules. The elution profile of the hybridized test fragment can be compared to a control in which a wild type fragment is hybridized to another wild type fragment. However, in some cases, only two peaks or partially resolved peaks are observed in DHPLC analysis. The two homoduplex peaks may appear as one peak or a partially resolved peak and the two heteroduplex peaks may appear as one peak or a partially resolved peak. In some cases, only a broadening of the initial peak is observed. Any change in the elution profile (such as the appearance of new peaks or shoulders) between the hybridized test fragment and the control is assumed to be due to a mutation in the test fragment.

FIG. 1 illustrates the temperature dependent separation of a mixture of homoduplexes and heteroduplexes by DHPLC. The data in FIG. 1 were obtained from a mixture containing both 209 bp homoduplex mutant and 209 bp homoduplex wild type species. Such "mutation standards" provide a mixture of DNA species that when hybridized and analyzed by DHPLC, produce previously characterized mutation separation profiles which can be used to evaluate the performance of the chromatography system. Mutation standards can be obtained commercially (e.g. a WAVE Optimized™ UV 209 bp Mutation Standard (part no. 700210), GCH338 Mutation Standard (part no.700215), and HTMS219 Mutation Standard (part no.700220) are available from Transgenomic, Inc. and a 209 bp mutation standard is also available from Varian, Inc.). Prior to injection of the mixture onto the separation column, the mutation standard was hybridized as shown in the scheme 100. The hybridization process created two homoduplexes and two heteroduplexes. As shown in the mutation separation profile 102, the hybridization product was separated using DHPLC. The two lower retention time peaks represent the two heteroduplexes and the two higher retention time peaks represent the two homoduplexes. The two homoduplexes separate because the A-T base pair denatures at a lower temperature than the C-G base pair. Without wishing to be bound by theory, the results are consistent with a greater degree of denaturation in one duplex and/or a difference in the polarity of one partially denatured heteroduplex compared to the other, resulting in a difference in retention time on the reverse-phase separation column.

A DHPLC system is capable of characterizing the melting behavior of a DNA fragment by running a series of separations at incrementally increasing temperatures over the entire likely denaturation range (e.g. 50°–70° C.) (as exemplified by FIG. 2).

Figure 2:
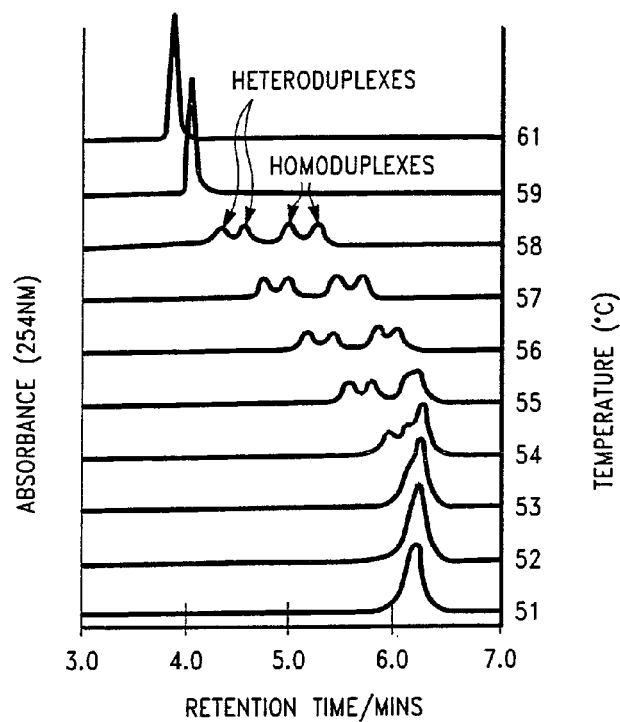
FIG. 2 illustrates the temperature dependent separation of homoduplex and heteroduplex molecules.

The temperature dependent separation of 209 base pair homoduplexes and heteroduplexes by DHPLC is shown in the elution profile 102 in FIG. 2 as a series of separation chromatograms and the separation process is described in Example 1. The sample, containing a heterozygous sample of 209 base pair homoduplex fragments wherein the mutant fragments contained a single base pair deviation from the wild type, was hybridized as described in Example 1. The hybridization process created 2 homoduplexes and 2 heteroduplexes as shown schematically in FIG. 1.

When DHPLC was performed at 51° C., a single peak, representing all 4 mixture components, was seen. This result was expected since all 4 components have the same base pair length and the separation was performed at non-denaturing conditions, i.e., at a temperature too low to cause any denaturing. At 53° C. a shoulder appeared on the low retention time side of the main peak. This indicated the beginning of melting as well the potential presence of heteroduplex and the partial separation of a heteroduplex. As the temperature of the separation was increased incrementally, the original single peak was eventually separated into 4 clearly defined peaks. The 2 lower retention time peaks representing the 2 heteroduplexes and the 2 higher retention time peaks representing the 2 homoduplexes. The two homoduplexes separate because the A-T base pair denatures at a lower temperature than the C-G base pair. Without wishing to be bound by theory, the results are consistent with a greater degree of denaturation in one duplex and/or a difference in the polarity of one partially denatured heteroduplex compared to the other, resulting in a difference in retention time on the DHPLC column.

As seen in FIG. 2, the temperature range of 57° to 58° C. was optimal for this separation. The appearance of four distinct peaks was observed when a mutation was present in the original sample, in agreement with the expected results, based on the hybridization schematic 100 in FIG. 1. Above that temperature the double stranded fragments are completely denatured, rather than being denatured only at the site of base pair mismatch. This is evidenced by the single peak, representing four single polynucleotide strands, seen at low retention time when the separation was carried out at 59° C. and above.

In preparing a set of DNA fragments for analysis by DHPLC, it is usually assumed that all of the fragments have the same length since they are generated using the same set of PCR primers. It is further usually assumed that the fragments are eluted under essentially the same conditions of temperature and solvent gradient. The pattern or shape of the mutation separation profile consists of peaks representing the detector response as various species elution during the separation process. The profile is determined by, for example, the number, height, width, symmetry and retention time of peaks. Other patterns can be observed, such as 3 or 2 peaks. The profile can also include poorly resolved shoulders. The shape of the profile contains useful information about the nature of the sample. The pattern or shape of the resulting chromatogram will be influenced by the type and location of the mutation. Each mutation (e.g. single nucleotide polymorphism (SNP)) has a corresponding elution profile, or signature, at a given set of elution conditions of temperature and gradient.

Detection of unknown mutations requires a highly sensitive, reproducible and accurate analytical method. The design of polymerase chain reaction (PCR) primers used to amplify DNA samples which are to be analyzed for the presence of mutations is an important factor contributing to accuracy, sensitivity and reliability of mutation detection. The design of primers specifically for the purpose of enhancing and optimizing mutation detection by DHPLC is disclosed in U.S. Pat. No. 6,287,822, the PCT publication WO9907899, by Xiao et al. (Human Mutation 17:439–474 (2001) and by Kuklin et al., (Genet. Test. 1:201–206 (1998).

Mutation detection of dsDNA using DHPLC is more reliable and accurate if the mutation is located within a section having a narrow midpoint temperature range. An example of such a section is the constant melting domain as described by Lerman et al. (Meth. Enzymol. 155:482 (1987)).

When the sequence of a DNA fragment to be amplified by PCR is known, commercially available software can be used to design primers which will produce either the whole fragment, or any section, within the fragment.

The primers for use in DHPLC are preferably selected to amplify a section of the target DNA fragment in which the bases have a narrow range of melting point. For example, the range can be less that about 15° C.

Generally, a fragment, such as an exon, will contain sample sequences, or sections, having different melting temperatures, but which have a narrow range of variation within any one section.

In preparing a sample for DHPLC, a selected section of a target DNA fragment is amplified by PCR using both forward and reverse primers which flank the first and second ends of the section. The amplification product is then hybridized with corresponding wild type double stranded DNA prior to analysis.

A "biological sample" is a sample of material derived from an organism.

As used herein "obtaining" a sample that includes, or that may include, an analyte polynucleotide can mean either obtaining from a biological source such as mammalian tissue, plant, or microbe, or obtaining from a reagent depository, such as a commercial vendor. When a sample is obtained from an animal or a human it will be understood that any number of appropriate means familiar to those having ordinary skill in the art can be employed. For example, if a blood sample is obtained, it can be obtained either by drawing blood through venepuncture, but also can be obtained as a forensic sample.

The term "mutation separation profile" is defined herein to include a separation chromatogram from a DHPLC (or tcDHPLC) analysis. If the injected sample contains heteroduplex and homoduplex molecules, the mutation separation profile shows the separation, or at least partial separation, of heteroduplexes from homoduplexes. Such profiles are characteristic of samples which contain mutations or polymorphisms and have been hybridized prior to chromatographic separation. The mutation separation profile 102 shown in FIG. 1 exemplifies a mutation separation profile as defined herein.

In some aspects, the present invention involves nucleic acid amplification procedures, such as PCR, which involve chain elongation by a DNA polymerase. There are a variety of different PCR techniques which utilize DNA polymerase enzymes, such as Taq polymerase. See PCR Protocols: A Guide to Methods and Applications. (Innis, M, Gelfand, D., Sninsky, J. and White, T., eds.), Academic Press, San Diego (1990) for detailed description of PCR methodology. PCR is also described in detail in U.S. Pat. No. 4,683,202 to Mullis (1987); Eckert et al., The Fidelity of DNA polymerases Used In The Polymerase Chain Reactions, McPherson, Quirke, and Taylor (eds.), "PCR: A Practical Approach", IRL Press, Oxford, Vol.1, pp. 225–244; Current Protocols in Molecular Biology, Ausubel et al. eds. John Wiley & Sons (1995), Chapter 15; and Andre, et. al., GENOME RESEARCH, Cold Spring Harbor Laboratory Press, pp. 843–852 (1977).

In a typical PCR protocol, a target nucleic acid, two oligonucleotide primers (one of which anneals to each strand), nucleotides, polymerase and appropriate salts are mixed and the temperature is cycled to allow the primers to anneal to the template, the DNA polymerase to elongate the primer, and the template strand to separate from the newly synthesized strand. Subsequent rounds of temperature cycling allow exponential amplification of the region between the primers.

There are a variety of different DNA polymerase enzymes that can be used in PCR, although proof-reading polymerases are preferred. DNA polymerases useful in the present invention may be any polymerase capable of replicating a DNA molecule. Preferred DNA polymerases are thermostable polymerases, which are especially useful in PCR. Thermostable polymerases are isolated from a wide variety of thermophilic bacteria, such as *Thermus aquaticus* (Taq), *Thermus brockianus* (Tbr), *Thermus flavus* (Tfl), *Thermus ruber* (Tru), *Thermus thermophilus* (Tth), *Thermococcus litoralis* (Tli) and other species of the Thermococcus genus, *Thermoplasma acidophilum* (Tac), *Thermotoga neapolitana* (Tne), *Thermotoga maritima* (Tma), and other species of the Thermotoga genus, *Pyrococcus furiosus* (Pfu), *Pyrococcus horikoshii* (Pho), *Pyrococcus woesei* (Pwo) and other species of the Pyrococcus genus, *Bacillus sterothermophilus* (Bst), *Sulfolobus acidocaldarius* (Sac) *Sulfolobus solfataricus* (Sso), *Pyrodictium occultum* (Poc), *Pyrodictium abyssi* (Pab), and *Methanobacterium thermoautotrophicum* (Mth), and mutants, variants or derivatives thereof.

Several DNA polymerases are known in the art and are commercially available (e.g., from Boehringer Mannheim Corp., Indianapolis, Ind.; Life Technologies, Inc., Rockville, Md.; New England Biolabs, Inc., Beverley, Mass.; Perkin Elmer Corp., Norwalk, Conn.; Pharmacia LKB Biotechnology, Inc., Piscataway, N.J.; Qiagen, Inc., Valencia, Calif.; Stratagene, La Jolla, Calif.; Transgenomic, Omaha, Nebr.). Preferably the thermostable DNA polymerase is selected from the group of Taq, Tbr, Tfl, Tru, Tth, Tli, Tac, Tne, Tma, Tih, Tfi, Pfu, Pwo, Kod, Bst, Sac, Sso, Poc, Pab, Mth, Pho, ES4, VENT™, DEEPVENT™, PFUTurbo™, AmpliTaq®, and active mutants, variants and derivatives thereof. It is to be understood that a variety of DNA polymerases may be used in the present invention, including DNA polymerases not specifically disclosed above, without departing from the scope or preferred embodiments thereof.

The PCR preferably utilizes buffers and other solutions that are compatible with DHPLC analysis, as described in U.S. patent application Ser. No. 10/126,848, filed Apr. 19, 2002. The PCR buffers, enzymes preparations, and other solutions minimize, or preferably exclude, BSA, mineral oil, formamide, polyethylene glycol, detergents such as Triton X-100, NP40, Tween 20, sodium dodecyl sulfate and sodium lauryl sulfate. Other reagents, such as those commonly used in the purification of DNA, such as proteases, solvents, nucleases, phenol, guanidinium, etc., are preferably removed in a final ethanol precipitation and wash step prior to PCR. Excess EDTA, isopropanol, or iso-amyl alcohol are also preferably removed. Examples of suitable proof reading enzyme preparations includes Pho polymerase (available as Optimase™ polymerase (Transgenomic) and AccuType™ DNA polymerase (Stratagene).

In a typical PCR protocol, a target nucleic acid, two oligonucleotide primers (one of which anneals to each strand), nucleotides, polymerase and appropriate salts are mixed and the temperature is cycled to allow the primers to anneal to the template, the DNA polymerase to elongate the primer, and the template strand to separate from the newly synthesized strand. Subsequent rounds of temperature cycling allow exponential amplification of the region between the primers.

Oligonucleotide primers useful in the present invention may be any oligonucleotide of two or more nucleotides in length. Preferably, PCR primers are about 15 to about 30 bases in length, and are not palindromic (self-complementary) or complementary to other primers that may be used in the reaction mixture. Oligonucleotide primers are oligonucleotides used to hybridize to a region of a target nucleic acid to facilitate the polymerization of a complementary nucleic acid. Any primer may be synthesized by a practitioner of ordinary skill in the art or may be purchased from any of a number of commercial venders (e.g., from Boehringer Mannheim Corp., Indianapolis, Ind.; New England Biolabs, Inc., Beverley, Mass.; Pharmacia LKB Biotechnology, Inc., Piscataway, N.J.). It will be recognized that the PCR primers can include covalently attached groups, such as fluorescent tags. U.S. Pat. No. 6,210,885 describes the use of such tags in mutation detection by DHPLC. It is to be understood that a vast array of primers may be useful in the present invention, including those not specifically disclosed herein, without departing from the scope or preferred embodiments thereof.

Buffering agents and salts are used in the PCR buffers and storage solutions of the present invention to provide appropriate stable pH and ionic conditions for nucleic acid synthesis, e.g., for DNA polymerase activity, and for the hybridization process. A wide variety of buffers and salt solutions and modified buffers are known in the art that may be useful in the present invention, including agents not specifically disclosed herein. Preferred buffering agents include, but are not limited to, TRIS, TRICINE, BIS-TRICINE, HEPES, MOPS, TES, TAPS, PIPES, CAPS. Preferred salt solutions include, but are not limited to solutions of; potassium acetate, potassium sulfate, ammonium sulfate, ammonium chloride, ammonium acetate, magnesium chloride, magnesium acetate, magnesium sulfate, manganese chloride, manganese acetate, manganese sulfate, sodium chloride, sodium acetate, lithium chloride, and lithium acetate.

The length and diameter of the separation column, as well as the system mobile phase pressure and temperature, and other parameters, can be varied. An increase in the column diameter was found to increase resolution of polynucleotide fragments in IP-RP-HPLC and DHPLC (U.S. Pat. No. 6,372,142; WO 01/19485). Size-based separation of DNA fragments can also be performed using batch methods and devices as disclosed in U.S. Pat. Nos. 6,265,168; 5,972,222; and 5,986,085.

In DHPLC, the mobile phase typically contains an ion-pairing agent (i.e. a counter ion agent) and an organic solvent. Ion-pairing agents for use in the method include lower primary, secondary and tertiary amines, lower trialkylammonium salts such as triethylammonium acetate and lower quaternary ammonium salts. Typically, the ion-pairing reagent is present at a concentration between about 0.05 and 1.0 molar. Organic solvents for use in the method include solvents such as methanol, ethanol, 2-propanol, acetonitrile, and ethyl acetate.

In one embodiment of DHPLC, the mobile phase for carrying out the separation contains less than about 40% by volume of an organic solvent and greater than about 60% by volume of an aqueous solution of the ion-pairing agent. In a preferred embodiment, elution is carried out using a binary gradient system.

Partial denaturation of heteroduplex molecules can be carried out in a variety of ways such as alteration of pH or salt concentration, use of denaturing agents, or elevation in temperature. Temperatures for carrying out the separation are typically between about 50° and 70° C. and preferably between about 550 and 65° C. The preferred temperature is sequence dependent. In carrying out a separation of GC-rich heteroduplex and homoduplex molecules, for example, a higher temperature is preferred.

A variety of liquid chromatography systems are available that can be used for conducting DHPLC. These systems typically include software for operating the chromatography components, such as pumps, heaters, mixers, fraction collection devices, injector. Examples of software for operating a chromatography apparatus include HSM Control System (Hitachi), ChemStation (Agilent), VP data system (Shimadzu), Millennium32 Software (Waters), Duo-Flow software (Bio-Rad), and Star workstation (Varian). Examples of preferred liquid chromatography systems for carrying out DHPLC include the WAVE® DNA Fragment Analysis System (Transgenomic) and the Varian ProStar Helix™ System (Varian).

In carrying out DHPLC analysis, the operating temperature and the mobile phase composition can be determined by trial and error. However, these parameters are preferably obtained using software. Computer software that can be used in carrying out DHPLC is disclosed in the following patents and patent applications: U.S. Pat. Nos. 6,287,822; 6,197,516; U.S. patent application Ser. No. 09/469,551 filed Dec. 22, 1999; and in WO0146687 and WO0015778. Examples of software for predicting the optimal temperature for DHPLC analysis are disclosed by Jones et al. in Clinical Chem. 45:113–1140 (1999) and in the website having the address of http://insertion.stanford.edu/melt.html. Examples of a commercially available software include WAVE-Maker® software and Navigator™ software (Transgenomic).

The IP-RP-HPLC retention times of double stranded DNA fragments can be predicted using software such as Wavemaker™ software (Transgenomic) or Star workstation software (Varian). These programs allow prediction of the retention time based on the length of a DNA fragment for a given set of elution conditions (U.S. Pat. Nos. 6,287,822 and 6,197,516; and in U.S. patent application Ser. No. 09/469,551 filed Dec. 22, 1999; and PCT publications WO99/07899 and WO 01/46687).

Suitable separation media for performing DHPLC are described in the following U.S. Pat. Nos. 6,379,889; 6,056,877; 6,066,258; 5,453,185; 5,334,310; U.S. patent application Ser. No. 09/493,734 filed Jan. 28, 2000; U.S. patent application Ser. No. 09/562,069 filed May 1, 2000; and in the following PCT applications: WO98/48914; WO98/48913; PCT/US98/08388; PCT/US00/11795. An example of a suitable column based on a polymeric stationary support is the DNASep® column (Transgenomic). Examples of suitable columns based on a silica stationary support include the Microsorb Analytical column (Varian and Rainin) and "ECLIPSE dsDNA" (Hewlett Packard, Newport, Del.).

Ion-Pairing Reversed-Phase Chromatography (IP-RPC) is a powerful form of chromatography used in the separation and analysis of polynucleotides, including DNA (both single and double stranded) and RNA (Eriksson et al., (1986) *J. Chromatography* 359:265–74). Most reported applications of IP-RPC have been in the context of high performance liquid chromatography (IP-RP-HPLC), but the technology can be accomplished using non-HPLC chromatography systems (U.S. patent application Ser. Nos. 09/318,407 and 09/391,963. Nevertheless, for the sake of simplicity much of the following description will focus on the use of IP-RP-HPLC, a particularly powerful and convenient form of IP-RPC. It is to be understood that this is not intended to limit the scope of the invention, and that generally the methods described can be performed without the use of HPLC, although this will in some cases lead to less than optimal results. IP-RPC is a form of chromatography characterized by the use of a reversed phase (i.e., hydrophobic) stationary phase and a mobile phase that includes an alkylated cation (e.g., triethylammonium) that is believed to form a bridging interaction between the negatively charged polynucleotide and non-polar stationary phase. The alkylated cation-mediated interaction of polynucleotide and stationary phase can be modulated by the polarity of the mobile phase, conveniently adjusted by means of a solvent that is less polar than water, e.g., acetonitrile. In general, a polynucleotide such as DNA or RNA is retained by the separation medium in the presence of counterion agent, and can be eluted by increasing the concentration of a non-polar solvent. Elution can be accomplished in the presence or absence of counterion agent. Performance is enhanced by the use of a non-porous separation medium, as described in U.S. patent application Ser. No. 5,585,236. Matched Ion Polynucleotide Chromatography (MIPC), is described in U.S. Pat. Nos. 5,585,236, 6,066,258 and 6,056,877 and PCT Publication Nos. WO98/48913, WO98/48914, WO/9856797, WO98/56798, incorporated herein by reference in their entirety. MIPC is characterized by the preferred use of solvents, chromatographic surfaces, and other surfaces in the mobile phase flow path that are substantially free of multivalent cation contamination that can interfere with polynucleotide separation. In the practice of the instant invention, a preferred system for performing MIPC separations is that provided by Transgenomic, Inc. under the trademark WAVE®.

Separation by IP-RP-HPLC, including DHPLC, occurs at the non-polar surface of a separation medium. In one embodiment, the non-polar surfaces comprise the surfaces of polymeric beads. In an alternative embodiment, the surfaces comprise the surfaces of interstitial spaces in a molded polymeric monolith, described in more detail infra. For purposes of simplifying the description of the invention and not by way of limitation, the separation of polynucleotides using nonporous beads, and the preparation of such beads, will be primarily described herein, it being understood that other separation surfaces, such as the interstitial surfaces of polymeric monoliths, are intended to be included within the scope of this invention.

In general, in order to be suitable for use in IP-RP-HPLC a separation medium should have a surface that is either intrinsically non-polar or bonded with a material that forms a surface having sufficient non-polarity to interact with a counterion agent.

DHPLC detection can be accomplished using a column filled with nonporous polymeric beads having an average diameter of about 0.5–100 microns; preferably, 1–10 microns; more preferably, 1–5 microns. Beads having an average diameter of 1.0–3.0 microns are most preferred.

In a preferred embodiment, the chromatographic separation medium comprises nonporous beads, i.e., beads having a pore size that essentially excludes the polynucleotides being separated from entering the bead, although porous beads can also be used. As used herein, the term "nonporous" is defined to denote a bead that has surface pores having a diameter that is sufficiently small so as to effectively exclude the smallest DNA fragment in the separation in the solvent medium used therein. Included in this definition are polymer beads having these specified maximum size restrictions in their natural state or which have been treated to reduce their pore size to meet the maximum effective pore size required.

The surface conformations of nonporous beads of the present invention can include depressions and shallow pit-like structures that do not interfere with the separation process. A pretreatment of a porous bead to render it nonporous can be effected with any material which will fill the pores in the bead structure and which does not significantly interfere with the IP-RP-HPLC process.

Pores are open structures through which mobile phase and other materials can enter the bead structure. Pores are often interconnected so that fluid entering one pore can exit from another pore. Without intending to be bound by any particular theory, it is believed that pores having dimensions that allow movement of the polynucleotide into the interconnected pore structure and into the bead impair the resolution of separations or result in separations that have very long retention times.

Non-porous polymeric beads useful in the practice of the present invention can be prepared by a two-step process in which small seed beads are initially produced by emulsion polymerization of suitable polymerizable monomers. The emulsion polymerization procedure is a modification of the procedure of Goodwin, et al. (*Colloid & Polymer Sci.*, 252:464–471 (1974)). Monomers which can be used in the emulsion polymerization process to produce the seed beads include styrene, alkyl substituted styrenes, alpha-methyl styrene, and alkyl substituted alpha-methyl styrene. The seed beads are then enlarged and, optionally, modified by substitution with various groups to produce the nonporous polymeric beads of the present invention.

The seed beads produced by emulsion polymerization can be enlarged by any known process for increasing the size of the polymer beads. For example, polymer beads can be enlarged by the activated swelling process disclosed in U.S. Pat. No. 4,563,510. The enlarged or swollen polymer beads are further swollen with a crosslinking polymerizable monomer and a polymerization initiator. Polymerization increases the crosslinking density of the enlarged polymeric bead and reduces the surface porosity of the bead. Suitable crosslinking monomers contain at least two carbon-carbon double bonds capable of polymerization in the presence of an initiator. Preferred crosslinking monomers are divinyl monomers, preferably alkyl and aryl (phenyl, naphthyl, etc.) divinyl monomers and include divinyl benzene, butadiene, etc. Activated swelling of the polymeric seed beads is useful to produce polymer beads having an average diameter ranging from 1 up to about 100 microns.

Alternatively, the polymer seed beads can be enlarged simply by heating the seed latex resulting from emulsion polymerization. This alternative eliminates the need for activated swelling of the seed beads with an activating solvent. Instead, the seed latex is mixed with the crosslinking monomer and polymerization initiator described above, together with or without a water-miscible solvent for the crosslinking monomer. Suitable solvents include acetone, tetrahydrofuran (THF), methanol, and dioxane. The resulting mixture is heated for about 1–12 hours, preferably about 4–8 hours, at a temperature below the initiation temperature of the polymerization initiator, generally, about 10° C.–80° C., preferably 30° C.–60° C. Optionally, the temperature of the mixture can be increased by 10–20% and the mixture heated for an additional 1 to 4 hours. The ratio of monomer to polymerization initiator is at least 100:1, preferably in the range of about 100:1 to about 500:1, more preferably about 200:1 in order to ensure a degree of polymerization of at least 200. Beads having this degree of polymerization are sufficiently pressure-stable to be used in HPLC applications. This thermal swelling process allows one to increase the size of the bead by about 110–160% to obtain polymer beads having an average diameter up to about 5 microns, preferably about 2–3 microns. The thermal swelling procedure can, therefore, be used to produce smaller particle sizes previously accessible only by the activated swelling procedure.

Following thermal enlargement, excess crosslinking monomer is removed and the particles are polymerized by exposure to ultraviolet light or heat. Polymerization can be conducted, for example, by heating of the enlarged particles to the activation temperature of the polymerization initiator and continuing polymerization until the desired degree of polymerization has been achieved. Continued heating and polymerization allows one to obtain beads having a degree of polymerization greater than 500.

For use in DHPLC (and tcDHPLC), packing material disclosed by U.S. Pat. No. 4,563,510 can be modified through substitution of the polymeric beads with alkyl groups or can be used in its unmodified state. For example, the polymer beads can be alkylated with 1 or 2 carbon atoms by contacting the beads with an alkylating agent, such as methyl iodide or ethyl iodide. Alkylation can be achieved by mixing the polymer beads with the alkyl halide in the presence of a Friedel-Crafts catalyst to effect electrophilic aromatic substitution on the aromatic rings at the surface of the polymer blend. Suitable Friedel-Crafts catalysts are well-known in the art and include Lewis acids such as aluminum chloride, boron trifluoride, tin tetrachloride, etc. The beads can be hydrocarbon substituted by substituting the corresponding hydrocarbon halide for methyl iodide in the above procedure, for example.

The term "alkyl" as used herein in reference to the beads useful in the practice of the present invention is defined to include alkyl and alkyl substituted aryl groups, having from 1 to 1,000,000 carbons, the alkyl groups including straight chained, branch chained, cyclic, saturated, unsaturated non-ionic functional groups of various types including aldehyde, ketone, ester, ether, alkyl groups, and the like, and the aryl groups including as monocyclic, bicyclic, and tricyclic aromatic hydrocarbon groups including phenyl, naphthyl, and the like. Methods for alkyl substitution are conventional and well-known in the art and are not an aspect of this invention. The substitution can also contain hydroxy, cyano, nitro groups, or the like which are considered to be non-polar, reverse phase functional groups.

Non-limiting examples of base polymers suitable for use in producing such polymer beads include mono- and di-vinyl substituted aromatics such as styrene, substituted styrenes, alpha-substituted styrenes and divinylbenzene; acrylates and methacrylates; polyolefins such as polypropylene and polyethylene; polyesters; polyurethanes; polyamides; polycarbonates; and substituted polymers including fluorosubstituted ethylenes commonly known under the trademark TEFLON. The base polymer can also be mixtures of polymers, non-limiting examples of which include poly(styrene-divinylbenzene) and poly(ethylvinylbenzene-divinylbenzene). Methods for making beads from these polymers are conventional and well known in the art (for example, see U.S. Pat. No. 4,906,378). The physical properties of the surface and near-surface areas of the beads are the primary determinant of chromatographic efficiency. The polymer, whether derivatized or not, should provide a nonporous, non-reactive, and non-polar surface for the separation. In a particularly preferred embodiment of the invention, the separation medium consists of octadecyl modified, nonporous alkylated poly(styrene-divinylbenzene) beads. Separation columns employing these particularly preferred beads, referred to as DNASep® columns, are commercially available from Transgenomic, Inc.

A separation bead used in the invention can comprise a nonporous particle which has non-polar molecules or a non-polar polymer attached to or coated on its surface. In general, such beads comprise nonporous particles which have been coated with a polymer or which have substantially all surface substrate groups reacted with a non-polar hydrocarbon or substituted hydrocarbon group, and any remaining surface substrate groups endcapped with a tri(lower alkyl)chlorosilane or tetra(lower alkyl)dichlorodisilazane as described in U.S. Pat. No. 6,056,877.

The nonporous particle is preferably an inorganic particle, but can be a nonporous organic particle. The nonporous particle can be, for example, silica, silica carbide, silica nitrite, titanium oxide, aluminum oxide, zirconium oxide, carbon, insoluble polysaccharides such as cellulose, or diatomaceous earth, or any of these materials which have been modified to be nonporous. Examples of carbon particles include diamond and graphite which have been treated to remove any interfering contaminants. The preferred particles are essentially non-deformable and can withstand high pressures. The nonporous particle is prepared by known procedures. The preferred particle size is about 0.5–100 microns; preferably, 1–10 microns; more preferably, 1–5 microns. Beads having an average diameter of 1.0–3.0 microns are most preferred.

Because the chemistry of preparing conventional silica-based reverse phase HPLC materials is well-known, most of the description of non-porous beads suitable for use in the instant invention is presented in reference to silica. It is to be understood, however, that other nonporous particles, such as those listed above, can be modified in the same manner and substituted for silica. For a description of the general chemistry of silica, see Poole, Colin F. and Salwa K. Poole, *Chromatography Today,* Elsevier: New York (1991), pp. 313–342 and Snyder, R. L. and J. J. Kirkland, *Introduction to Modern Liquid Chromatography,* $2^{nd}$ ed., John Wiley & Sons, Inc.: New York (1979), pp. 272–278, the disclosures of which are hereby incorporated herein by reference in their entireties.

The nonporous beads of the invention are characterized by having minimum exposed silanol groups after reaction with the coating or silating reagents. Minimum silanol groups are needed to reduce the interaction of the DNA with the substrate and also to improve the stability of the material in a high pH and aqueous environment. Silanol groups can be harmful because they can repel the negative charge of the DNA molecule, preventing or limiting the interaction of the DNA with the stationary phase of the column. Another possible mechanism of interaction is that the silanol can act as ion exchange sites, taking up metals such as iron (III) or chromium (III). Iron (III) or other metals which are trapped on the column can distort the DNA peaks or even prevent DNA from being eluted from the column.

Silanol groups can be hydrolyzed by the aqueous-based mobile phase. Hydrolysis will increase the polarity and reactivity of the stationary phase by exposing more silanol sites, or by exposing metals that can be present in the silica core. Hydrolysis will be more prevalent with increased underivatized silanol groups. The effect of silanol groups on the DNA separation depends on which mechanism of interference is most prevalent. For example, iron (III) can become attached to the exposed silanol sites, depending on whether the iron (III) is present in the eluent, instrument or sample.

The effect of metals can only occur if metals are already present within the system or reagents. Metals present within the system or reagents can get trapped by ion exchange sites on the silica. However, if no metals are present within the system or reagents, then the silanol groups themselves can cause interference with DNA separations. Hydrolysis of the exposed silanol sites by the aqueous environment can expose metals that might be present in the silica core.

Fully hydrolyzed silica contains a concentration of about 8μ moles of silanol groups per square meter of surface. At best, because of steric considerations, a maximum of about 4.5 μmoles of silanol groups per square meter can be reacted, the remainder of the silanol being sterically shielded by the reacted groups. Minimum silanol groups is defined as reaching the theoretical limit of or having sufficient shield to prevent silanol groups from interfering with the separation.

Numerous methods exist for forming nonporous silica core particles. For example, sodium silicate solution poured into methanol will produce a suspension of finely divided spherical particles of sodium silicate. These particles are neutralized by reaction with acid. In this way, globular particles of silica gel are obtained having a diameter of about 1–2 microns. Silica can be precipitated from organic liquids or from a vapor. At high temperature (about 2000° C.), silica is vaporized, and the vapors can be condensed to form finely divided silica either by a reduction in temperature or by using an oxidizing gas. The synthesis and properties of silica are described by R. K. Iler in *The Chemistry of Silica, Solubility, Polymerization, Colloid and Surface Properties, and Biochemistry,* John Wiley & Sons: New York (1979). W. Stöber et al. described controlled growth of monodisperse silica spheres in the micron size range in *J. Colloid and Interface Sci.,* 26:62–69 (1968). Stöber et al. describe a system of chemical reactions which permit the controlled growth of spherical silica particles of uniform size by means of hydrolysis of alkyl silicates and subsequent condensation of silicic acid in alcoholic solutions. Ammonia is used as a morphological catalyst. Particle sizes obtained in suspension range from less than 0.05 µm to 2 µm in diameter.

To prepare a nonporous bead, the nonporous particle can be coated with a polymer or reacted and endcapped so that substantially all surface substrate groups of the nonporous particle are blocked with a non-polar hydrocarbon or substituted hydrocarbon group. This can be accomplished by any of several methods described in U.S. Pat. No. 6,056,877. Care should be taken during the preparation of the beads to ensure that the surface of the beads has minimum silanol or metal oxide exposure and that the surface remains nonporous. Nonporous silica core beads can be obtained from Micra Scientific (Northbrook, Ill.) and from Chemie Uetikkon (Lausanne, Switzerland).

Another example of a suitable stationary support is a wide pore silica-based alkylated support as described in U.S. Pat. No. 6,379,889.

In other embodiments, the IP-RP-HPLC separation medium can be in the form of a polymeric monolith, e.g., a rod-like monolithic column. A monolith is a polymer separation media, formed inside a column, having a unitary structure with through pores or interstitial spaces that allow eluting solvent and analyte to pass through and which provide the non-polar separation surface, as described in U.S. Pat. No. 6,066,258 and U.S. patent application Ser. No. 09/562,069. Monolithic columns, including capillary columns, can also be used, such as disclosed in U.S. Pat. No. 6,238,565; U.S. patent application Ser. No. 09/562,069 filed May 1, 2000; the PCT application WO00/15778; and by Huber et al (Anal. Chem. 71:3730–3739 (1999)). The interstitial separation surfaces can be porous, but are preferably nonporous. The separation principles involved parallel those encountered with bead-packed columns. As with beads, pores traversing the monolith must be compatible with and permeable to DNA. In a preferred embodiment, the rod is substantially free of contamination capable of reacting with DNA and interfering with its separation, e.g., multivalent cations.

A molded polymeric monolith rod that can be used in practicing the present invention can be prepared, for example, by bulk free radical polymerization within the confines of a chromatographic column. The base polymer of the rod can be produced from a variety of polymerizable monomers. For example, the monolithic rod can be made from polymers, including mono- and di-vinyl substituted aromatic compounds such as styrene, substituted styrenes, alpha-substituted styrenes and divinylbenzene; acrylates and methacrylates; polyolefins such as polypropylene and polyethylene; polyesters; polyurethanes; polyamides; polycarbonates; and substituted polymers including fluorosubstituted ethylenes commonly known under the trademark TEFLON. The base polymer can also be mixtures of polymers, non-limiting examples of which include poly(glycidyl methacrylate-co-ethylene di methacrylate), poly(styrene-divinylbenzene) and poly(ethylvinylbenzene-divinylbenzene. The rod can be unsubstituted or substituted with a substituent such as a hydrocarbon alkyl or an aryl group. The alkyl group optionally has 1 to 1,000,000 carbons inclusive in a straight or branched chain, and includes straight chained, branch chained, cyclic, saturated, unsaturated nonionic functional groups of various types including aldehyde, ketone, ester, ether, alkyl groups, and the like, and the aryl groups includes as monocyclic, bicyclic, and tricyclic aromatic hydrocarbon groups including phenyl, naphthyl, and the like. In a preferred embodiment, the alkyl group has 1–24 carbons. In a more preferred embodiment, the alkyl group has 1–8 carbons. The substitution can also contain hydroxy, cyano, nitro groups, or the like which are considered to be non-polar, reverse phase functional groups. Methods for hydrocarbon substitution are conventional and well-known in the art and are not an aspect of this invention. The preparation of polymeric monoliths is by conventional methods well known in the art as described in the following references: Wang et al. (1994) *J. Chromatog. A* 699:230; Petro et al. (1996) *Anal. Chem.* 68:315 and U.S. Pat. Nos. 5,334,310; 5,453,185 and 5,522,994. Monolith or rod columns are commercially available form Merck & Co (Darmstadt, Germany).

The separation medium can take the form of a continuous monolithic silica gel. A molded monolith can be prepared by polymerization within the confines of a chromatographic column (e.g., to form a rod) or other containment system. A monolith is preferably obtained by the hydrolysis and polycondensation of alkoxysilanes. A preferred monolith is derivatized in order to produce non-polar interstitial surfaces. Chemical modification of silica monoliths with ocatdecyl, methyl or other ligands can be carried out. An example of a preferred derivatized monolith is one which is polyfunctionally derivatized with octadecylsilyl groups. The preparation of derivatized silica monoliths can be accomplished using conventional methods well known in the art as described in the following references which are hereby incorporated in their entirety herein: U.S. Pat. No. 6,056,877, Nakanishi, et al., *J. Sol-Gel Sci. Technol.* 8:547 (1997); Nakanishi, et al., *Bull. Chem. Soc. Jpn.* 67:1327 (1994); Cabrera, et al., *Trends Analytical Chem.* 17:50 (1998); Jinno, et al., *Chromatographia* 27:288 (1989).

DHPLC (and tcDHPLC) is preferably conducted using a separation medium that is substantially free of metal contaminants or other contaminants that can bind nucleic acids or that can interfere with the separation. Preferred beads and monoliths have been produced under conditions where precautions have been taken to substantially eliminate any multivalent cation contaminants (e.g. Fe(III), Cr(III), or colloidal metal contaminants), including a decontamination treatment, e.g., an acid wash treatment. Very pure, non-metal containing materials are preferred in the production of the beads in order to minimize the metal content of the resulting beads.

In addition to the separation medium being substantially metal-free, to achieve optimum peak separation the separation column and all process solutions held within the column or flowing through the column are preferably substantially free of multivalent cation contaminants (e.g. Fe(III), Cr(III), and colloidal metal contaminants). As described in U.S. Pat. Nos. 5,772,889, 5,997,742 and 6,017,457, this can be achieved by supplying and feeding solutions that enter the separation column with components that have process solution-contacting surfaces made of material which does not release multivalent cations into the process solutions held within or flowing through the column, in order to protect the column from multivalent cation contamination. The process solution-contacting surfaces of the system components are preferably material selected from the group consisting of titanium, coated stainless steel, passivated stainless steel, and organic polymer. Metals found in stainless steel, for example, do not harm the separation, unless they are in an oxidized or colloidal partially oxidized state. For example, 316 stainless steel frits are acceptable in column hardware, but surface oxidized stainless steel frits harm the DNA separation.

Trace levels of multivalent cations anywhere in the solvent flow path can cause a significant deterioration in the resolution of the separation after multiple uses of an IP-RP-HPLC column. This can result in increased cost caused by the need to purchase replacement columns and increased downtime. Therefore, effective measures are preferably taken to prevent multivalent metal cation contamination of the separation system components, including separation media and mobile phase contacting. These measures include, but are not limited to, washing protocols to remove traces of multivalent cations from the separation media and installation of guard cartridges containing cation capture resins, in line between the mobile phase reservoir and the IP-RP-HPLC column. These, and similar measures, taken to prevent system contamination with multivalent cations have resulted in extended column life and reduced analysis downtime.

For additional protection, multivalent cations in mobile phase solutions and sample solutions entering the column can be removed by contacting these solutions with multivalent cation capture resin before the solutions enter the column to protect the separation medium from multivalent cation contamination. The multivalent capture resin is preferably cation exchange resin and/or chelating resin.

There are two places where multivalent-cation-binding agents, e.g., chelators, can be used in DHPLC separations. In one embodiment, these binding agents can be incorporated into a solid through which the mobile phase passes. Contaminants are trapped before they reach places within the system that can harm the separation. In these cases, the functional group is attached to a solid matrix or resin (e.g., a flow-through cartridge, usually an organic polymer, but sometimes silica or other material). The capacity of the matrix is preferably about 2 mequiv./g. An example of a suitable chelating resin is available under the trademark CHELEX 100 (Dow Chemical Co.) containing an iminodiacetate functional group.

In another embodiment, the multivalent cation-binding agent can be added to the mobile phase. The binding functional group is incorporated into an organic chemical structure. The preferred multivalent cation-binding agent fulfills three requirements. First, it is soluble in the mobile phase. Second, the complex with the metal is soluble in the mobile phase. Multivalent cation-binding agents such as EDTA fulfill this requirement because both the chelator and the multivalent cation-binding agent-metal complex contain charges, which makes them both water-soluble. Also, neither precipitate when acetonitrile, for example, is added. The solubility in aqueous mobile phase can be enhanced by attaching covalently bound ionic functionality, such as, sulfate, carboxylate, or hydroxy. A preferred multivalent cation-binding agent can be easily removed from the column by washing with water, organic solvent or mobile phase. Third, the binding agent must not interfere with the chromatographic process.

The multivalent cation-binding agent can be a coordination compound. Examples of preferred coordination compounds include water soluble chelating agents and crown ethers. Non-limiting examples of multivalent cation-binding agents which can be used in the present invention include acetylacetone, alizarin, aluminon, chloranilic acid, kojic acid, morin, rhodizonic acid, thionalide, thiourea, α-furildioxime, nioxime, salicylaldoxime, dimethylglyoxime, α-furildioxime, cupferron, α-nitroso-β-naphthol, nitroso-R-salt, diphenylthiocarbazone, diphenylcarbazone, eriochrome black T, PAN, SPADNS, glyoxal-bis(2-hydroxyanil), murexide, α-benzoinoxime, mandelic acid, anthranilic acid, ethylenediamine, glycine, triaminotriethylamine, thionalide, triethylenetetramine, EDTA, metalphthalein, arsonic acids, α,α'-bipyridine, 4-hydroxybenzothiazole, 8-hydroxyquinaldine, 8-hydroxyquinoline, 1,10-phenanthroline, picolinic acid, quinaldic acid, α,α',α''-terpyridyl, 9-methyl-2,3,7-trihydroxy-6-fluorone, pyrocatechol, salicylic acid, tiron, 4-chloro-1,2-dimercaptobenzene, dithiol, mercaptobenzothiazole, rubeanic acid, oxalic acid, sodium diethyldithiocarbarbamate, and zinc dibenzyldithiocarbamate. These and other examples are described by Perrin in *Organic Complexing Reagents: Structure, Behavior, and Application to Inorganic Analysis,* Robert E. Krieger Publishing Co. (1964). In the present invention, a preferred multivalent cation-binding agent is EDTA.

To achieve high-resolution chromatographic separations of polynucleotides, it is generally necessary to tightly pack the chromatographic column with the solid phase polymer beads. Any known method of packing the column with a column packing material can be used in the present invention to obtain adequate high-resolution separations. Typically, a slurry of the polymer beads is prepared using a solvent having a density equal to or less than the density of the polymer beads. The column is then filled with the polymer bead slurry and vibrated or agitated to improve the packing density of the polymer beads in the column. Mechanical vibration or sonication is typically used to improve packing density.

For example, to pack a 50×4.6 mm ID column, 2.0 grams of beads can be suspended in 10 ml of methanol with the aid of sonication. The suspension is then packed into the column using 50 mL of methanol at 8,000 psi of pressure. This improves the density of the packed bed.

There are several types of counterions suitable for use with IP-RP-HPLC. These include a mono-, di-, or trialkylamine that can be protonated to form a positive counter charge or a quaternary alkyl substituted amine that already contains a positive counter charge. The alkyl substitutions may be uniform (for example, triethylammonium acetate or tetrapropylammonium acetate) or mixed (for example, propyldiethylammonium acetate). The size of the alkyl group may be small (methyl) or large (up to 30 carbons) especially if only one of the substituted alkyl groups is large and the others are small. For example octyldimethylammonium acetate is a suitable counterion agent. Preferred counterion agents are those containing alkyl groups from the ethyl, propyl or butyl size range.

Without intending to be bound by any particular theory, it is believed the alkyl group functions by imparting a nonpolar character to the DNA through an ion pairing process so that the DNA can interact with the nonpolar surface of the separation media. The requirements for the degree of nonpolarity of the counterion-DNA pair depends on the polarity of the separation media, the solvent conditions required for separation, the particular size and type of fragment being separated. For example, if the polarity of the separation media is increased, then the polarity of the counterion agent may have to be adjusted to match the polarity of the surface and increase interaction of the counterion-DNA pair. In general, as the size and hydrophobicity of the alkyl group is increased, the separation is less influenced by DNA sequence and base composition, but rather is based predominately on DNA sequence length.

In some cases, it may be desired to increase the range of concentration of organic solvent used to perform the separation. For example, increasing the alkyl chain length on the counterion agent will increase the nonpolarity of the counterion-DNA pair resulting in the need to either increase the concentration of the mobile phase organic solvent, or increase the strength of the organic solvent type, e.g., acetonitrile is about two times more effective than methanol for eluting DNA. There is a positive correlation between concentration of the organic solvent required to elute a fragment from the column and the length of the fragment. However, at high organic solvent concentrations, the polynucleotide can precipitate. To avoid precipitation, a more non-polar organic solvent and/or a smaller counterion alkyl group can be used. The alkyl group on the counterion agent can also be substituted with halides, nitro groups, or the like to modulate polarity.

The mobile phase preferably contains a counterion (i.e. ion pairing) agent. Typical counterion agents include trialkylammonium salts of organic or inorganic acids, such as lower alkyl primary, secondary, and lower tertiary amines, lower trialkyammonium salts and lower quaternary alkylammonium salts. Lower alkyl refers to an alkyl radical of one to six carbon atoms, as exemplified by methyl, ethyl, n-butyl, i-butyl, t-butyl, isoamyl, n-pentyl, and isopentyl. Examples of counterion agents include octylammonium acetate, octadimethylammonium acetate, decylammonium acetate, octadecylammonium acetate, pyridiniumammonium acetate, cyclohexylammonium acetate, diethylammonium acetate, propylethylammonium acetate, propyldiethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetrapropylammonium acetate, and tetrabutylammonium acetate. Although the anion in the above examples is acetate, other anions may also be used, including carbonate, phosphate, sulfate, nitrate, propionate, formate, chloride, and bromide, or any combination of cation and anion. These and other agents are described by Gjerde, et al. in *Ion Chromatography, 2nd Ed.*, Dr. Alfred Hüthig Verlag Heidelberg (1987). In a particularly preferred embodiment of the invention the counterion is tetrabutylammonium bromide (TBAB) is preferred, although other quaternary ammonium reagents such as tetrapropyl or tetrabutyl ammonium salts can be used. Alternatively, a trialkylammonium salt, e.g., triethylammonium acetate (TEAA) can be used. The pH of the mobile phase is preferably within the range of about pH 5 to about pH 9, and optimally within the range of about pH 6 to about pH 7.5.

In DHPLC, it is routinely observed that each different DNA fragment being analyzed requires a different column temperature in order to reliably detect heteroduplexes. The required temperature depends on the sequence of the fragment and on the position of the mutation (U.S. Pat. No. 6,287,822). DHPLC will not detect the presence of heteroduplex molecules if the column temperature is not correctly set. As shown in FIG. 2, for example, in going from 58° C. to 59° C., the four peaks due to homoduplex and heteroduplex molecules completely disappeared.

The instant invention is based in part on the surprising discovery by Applicants that when certain nitrogen-containing additives are included in the mobile phase during DHPLC analysis, essentially any mixture of homoduplex and heteroduplex molecules can be analyzed at a single pre-selected column temperature. The homoduplex and heteroduplex molecules are prepared by a conventional hybridization process as described herein and are preferably in the size range of about 100 to about 1000 base pairs, and more preferably in the range of about 200 to about 500 base pairs. "Temperature-compression DHPLC" (tcDHPLC) is defined herein to include reference to the DHPLC method performed under conditions in which essentially any mixture of homoduplex and heterodulex molecules can be analyzed at a single pre-selected column temperature. The mixture can be derived from nucleic acids obtained from a biological source but can include synthetically prepared nucleic acids. tcDHPLC is preferably conducted using a mobile phase containing at least one of the nitrogen-containing additives as described herein. A preferred additive is betaine. The preferred size range of the DNA fragments for analysis by tcDHPLC is about 150 bp (base pairs) to about 1000 bp, and more preferably in the range of about 200 bp to about 500 bp. The pre-selected temperature will depend on the specific nitrogen-containing additive and its mobile phase concentration, as described herein. The temperature can be less than about 50° C. The use of such additives in tcDHPLC obviates the need to search empirically or to use software to obtain an optimal column temperature for the analysis.

Examples of suitable nitrogen-containing additives include, betaine, alkylammonium ions such as tetraalkylammonium ions, and choline. Without wishing to be bound by theory, Applicants believe that these additives can eliminate or reverse the dependence of DNA transition temperature (i.e. DNA melting temperature) on base composition.

In one aspect, the invention concerns a chromatographic method for separating heteroduplex and homoduplex DNA molecules in a mixture. The method includes (a) applying the mixture to a reverse phase separation medium, (b) eluting the medium of step (a) with a mobile phase comprising a nitrogen-containing additive, wherein the eluting is carried out under conditions effective to at least partially denature said heteroduplexes and wherein the eluting results in the separation, or at least partial separation, of said heteroduplxes from said homoduplexes. Examples of such compounds include nitrogen-containing additives as described herein. The eluting can be performed at a column temperature in the range of about 20° C. to about 80° C., and is preferably conducted at a column temperature of less than about 50° C., and more preferably in the range of about 30° C. to about 50° C., and optimally in the range of about 30° C. to less than about 50° C.

In another aspect, the invention provides a mobile phase useful in the elution of heteroduplex and homoduplex DNA molecules during tcDHPLC. The mobile phase preferably includes a nitrogen-containing additive as described herein. The mobile phase is preferably maintained at a temperature less than about 50° C. during tcDHPLC. A non-limiting example of a suitable mobile phase is an aqueous solution of 4M betaine, 100 mM TEAA, and 15% acetonitrile.

In yet another aspect, the invention concerns compositions that include the combination of the mobile phase containing a nitrogen-containing additive with a separation medium. Examples of a suitable separation medium includes reverse phase beads or a separation monolith having hydrophobic separation surfaces. In the combination, the mobile phase and separation medium are preferably maintained at a temperature less than about 50° C.

As a non-limiting example, three separate mutation standards required widely different temperatures for elution of heteroduplex molecules when analyzed using DHPLC with mobile phase lacking betaine (Example 2). Applicants selected a mobile phase concentration of betaine of 4M. At this concentration of betaine, Applicants surprisingly observed that the heteroduplexes for all three mutation standards could be detected (e.g. observed by visual inspection of the elution profiles) at a single temperature of 43° C. (Example 3).

Any of the separation media, solvents, or ion pairing agents for DHPLC, as described hereinabove, can be used in tcDHPLC. An advantage in using tcDHPLC is that it allows elution at temperatures below about 50° C. This is especially preferred when using silica based separation media, which are unstable at elevated temperatures.

In the use of the present invention, a suitable mobile phase concentration of any of the nitrogen-containing additives as described herein, and a corresponding column temperature for performing tcDHPLC analysis, can be readily selected by one skilled in the art, by analyzing known mixtures of heteroduplex and homoduplex molecules.

The following is an example of the selection of suitable mobile phase concentration for betaine. Three separate mutation standards (DYS271, HTM219, and GCH338 as described in Examples herein) were found to have different T(hsst) values when analyzed using DHPLC (with mobile phase lacking betaine). Applicants selected a concentration of betaine of 4M. At this concentration of betaine, Applicants surprisingly observed that the heteroduplexes for all three mutation standards could be observed (e.g. by visual inspection of the elution profiles) at a single temperature of 43° C.

In another example of the selection of a suitable mobile phase, Applicants observed that a HTM219 mutation standard had a T(hsst) of 70° C. when using mobile phase lacking betaine and a DYS271 mutation standard had a T(hsst) of 56° C. when using mobile phase lacking betaine. However, heteroduplexes from both mutation standards were detectable at the same column temperature of 43° C. when using a mobile phase containing 4M betaine. Essentially any mixture of heteroduplex and homoduplex molecules in the size range of about up to about 1000 base pairs, and preferably in the range of about 200 to about 500 base pairs, can be analyzed using this mobile phase and temperature. These two mutation standards span the limits of T(hsst) for substantially all nucleic acid fragments that are amenable to DHPLC analysis, including those obtained from a biological source. These two mutation standards can be used in establishing a pre-selected concentration of any nitrogen-containing additive, such as described herein, for conducting tcDHPLC. For example, at a betaine concentration of 2.5 M, a column temperature of 47° C. was found to be preferred in order to detect heteroduplexes for these two mutation standards. By graphically plotting required betaine concentration vs. column temperature, a linear mathematical relationship was observed. Many other suitable combinations of betaine concentration and temperature can be obtained from this relationship.

An analogous mathematical relationship can be obtained for the other nitrogen-containing additives described herein, thus allowing selection of a suitable mobile phase and temperature for tcDHPLC. Non-limiting examples of a suitable concentration of nitrogen-containing additive include: 3M tetramethylammonium chloride, 2.4 M tetraethylammonium chloride, and 3M triethylamine hydrochloride. The additive can be present at a fixed pre-selected concentration. In other embodiments, a shallow pre-selected gradient of additive can be used. An example of such a gradient is 3.5M betaine increasing to 4M betaine during the elution.

The mutation standards described in the Examples herein are merely illustrative. Other combinations of mutations standards could also be identified based on thousands of DNA fragments analyzed using the DHPLC method, and used as described herein, but preferred standards will span a range of T(hsst) of at least about 5° C. and more preferably at least about 10° C.

During tcDHPLC, all of the fragments in a mixture can be analyzed using the same gradient of organic solvent (e.g. acetonitrile). In other embodiments, in order to minimize the time required for analysis of multiple samples, the solvent gradient is adjusted so that all of the samples elute within a narrow range of retention time (e.g. between 5 and 6 min). There is a highly reproducible relationship between fragment length vs. % of buffer B (U.S. Pat. No. 6,287,822). This relationship was used to adjust the acetonitrile gradient so that all of the fragments eluted with retention times between about 5 and 6 min.

An advantage of using nitrogen-containing additives such as those described herein for conducting tcDHPLC is that the design of PCR amplicons is greatly simplified. For example, there is no need to place the mutation at a certain position or within a certain region of the amplicon. This is in contrast to conventional DHPLC in which it is preferred to localize the mutation in a "low melting" domain and within a certain distance from the end of the fragment (U.S. Pat. No. 6,287,822). In tcDHPLC, the mutation site can be located essentially anywhere within the fragment. The mutation is preferably positioned between the primers (i.e. is not located under a primer). Prior to the instant invention, PCR primers were preferably selected to locate a mutation in a preferred region of an amplicon (U.S. Pat. No. 6,287,822 and PCT publication WO99/07899) for DHPLC analysis. The present invention obviates the need for such primer design. Prior to the instant invention, it was preferred to incorporate GC clamps into PCR primers for certain difficult-to-detect mutations (U.S. Pat. No. 6,287,822; U.S. patent application Ser. No.10/033,104; PCT application nos. WO99/07899 and PCT/US01/45676). The present invention obviates the need for GC clamps, and therefore decreases costs and can facilitate the detection of mutations that had heretofore been difficult or impossible to observe.

As mentioned above, software employing mathematical models is often used to predict the temperature at which there is partial denaturation at a site of mismatch in each fragment, in order to allow detection by DHPLC. Additional empirical analysis is often required. Such predictions and additional experiments are not required in tcDHPLC. All nucleic acid fragments, within a selected size range, can be analyzed at the same temperature, thus simplifying the analysis.

An important aspect of the present invention concerns mobile phase additives that improve the detection of mutations in DNA. Non-limiting examples of nitrogen-containing additives suitable for use in tcDHPLC include compounds represented by the formula:

(I)

wherein:
$R^1$, $R^2$, and $R^3$, may be the same or different and are independently selected from the group consisting of hydrogen, methyl, ethyl, hydroxyethyl, and propyl, with the proviso that no more than two of $R^1$, $R^2$, and $R^3$ are hydrogen; and X is a moiety selected from the group consisting of:

radicals of the formulas

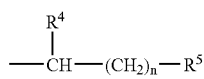

wherein:

$R^4$ is selected from the group consisting of methyl and hydrogen and, when combined with $R^1$, forms a pyrrolidine ring;

$R^5$ is selected from the group consisting of —$CO_2H$, —$CH_2OH$, and —$SO_3H$; and n is an integer of from 0 to 2; and with the proviso that, when $R^1$ and $R^4$ form a pyrrolidine ring, no more than one of $R^2$ and $R^3$ is hydrogen; and When a pyrrolidine ring is formed by $R^1$ and $R^4$, a compound of formula III is formed.

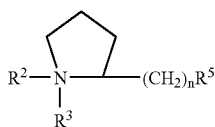

In certain preferred embodiments, the methods, compositions, and kits of the present invention include compounds of formula I wherein $R^1$, $R^2$, and $R^3$, may be the same or different and are independently selected from the group consisting of hydrogen, methyl, ethyl, and propyl, with the proviso that no more than two of $R^1$, $R^2$, and $R^3$ are hydrogen and, when $R^1$ and $R^4$ form a pyrrolidine ring, no more than one of $R^2$ and $R^3$ is hydrogen.

In another group of preferred embodiments, the methods, compositions, and kits of the present invention can include a compound of formula I wherein X is —$CH_2CO_2H$. Further preferred embodiments within this group use compounds where $R^1$, $R^2$ and $R^3$ are methyl; where $R^1$, $R^2$ are methyl and $R^3$ is hydrogen; or where $R^1$ is methyl and $R^2$ and $R^3$ are hydrogen.

In further preferred embodiments, the methods, compositions, and kits of the instant invention can utilize a compound of formula I wherein X is =O and $R^1$, $R^2$ and $R^3$ are methyl.

In still further preferred embodiments, the methods and kits of the invention can include a compound of formula I wherein $R^1$ and $R^4$ form a pyrrolidine ring, $R^2$ and $R^3$ are methyl, n is 0, and $R^5$ is —$CO_2H$ (stachydrine, formula IV).

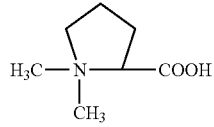

In yet another group of preferred embodiments, the methods and kits of this invention can include compounds where $R^1$, $R^2$ and $R^3$ are methyl and X is —$CH_2$—$SO_3H$ (sulfobetaine).

In general, the compounds as described herein are commercially available. For example, betaine, choline, dimethylglycine, sarcosine, and trimethylamine N-oxide can all be obtained from Sigma-Aldrich Corp.

These compounds may also be synthesized by routine methods known to those of skill in the art. For example, compounds of formula wherein $R^4$ is H, n is 0 and $R^5$ is —$CO_2H$ can be synthesized by the method of Lloyd, et al. (1992) J. Pharm. Pharmacol. 44:507–511. In general, ethyl chloroacetate is heated to reflux with the appropriate tertiary amine in ethanol. When the reaction is complete, the ethanol is removed from the reaction mixture by evaporation under reduced pressure. The residue is dissolved in 3–6% w/v aqueous HCl and warmed to reflux. Evaporation of the solvent under reduced pressure provides the desired products. Typically, these products can be recrystallized from an acetonitrile/water mixture.

Compounds of formula I wherein $R^4$ is H or $CH_3$, n is 1 and $R^5$ is $CO_2H$ can be synthesized by the method of Fiedorek, F. T., U.S. Pat. No. 2,548,428. In brief, betalactones are reacted with tertiary amines to provide the desired compounds.

Compounds of formula I wherein $R^4$ is H, n is 2, and $R^5$ is —$CO_2H$ can be synthesized by the method of Aksnes, G., et al. J. Chem. Soc. London 1959:103–107. In brief, 4-bromobutyric acid (Sigma-Aldrich) is converted to a methyl ester by treatment with methyl alcohol and catalytic sulfuric acid. Subsequent treatment of the methyl ester with excess alcoholic tertiary amine provides the desired compounds.

Compounds of formula I wherein $R^4$ and $R^1$ are taken together to form a pyrrolidine ring and where $R^5$ is $CO_2H$ are synthesized by the general method of Karer, et al. (1925) Helv. Chim. Acta. 8:364. For example, stachydrine is formed by the methylation of proline, according to this procedure.

Compounds of formula i wherein X is =O are synthesized by oxidation of the corresponding tertiary amines (see March, J. (1992) Advanced Organic Chemistry, Reactions, Mechanisms and Structure, Fourth Edition, John Wiley and Sons, New York, pp.1200–1201). Typically, the oxidation is carried out with hydrogen peroxide, but other peracids may also be used.

Compounds of formula I wherein X is →O include N-oxides. The "→" symbol indicates a dative bond.

Sulfobetaine can be synthesized according to the procedure of King, J. F., et al. (1985) J. Phosphorus Sulfur 25:11–20. Other compounds of formula I wherein $R^5$ is —$SO_3H$ can also be synthesized by modifications of this procedure and by other methods known to those of skill in the art.

Examples of preferred additives include betaine, bicine, choline, trimethylamine N-oxide, dimethylglycine, tetrapropylammoinium chloride (TPACl), tetraethylammonium chloride (TEACl), tetramethylammonium chloride (TMACl).

Some nitrogen-containing additives of the present invention may be present with a positive or negative charge or with both a positive and negative charges, depending on the pH of the solution. It is understood that these various forms of these additives are included in the present invention.

The term betaine, as used herein, refers to N,N,N-trimethylglycine.

The concentration of the additive in the mobile phase during DHPLC can be a selected value within the range from about 1 M to about 10M. Examples of preferred concentrations are in the range of about 1 to about 8M, and most preferably in the range of about 2M to about 5M. In some cases, the highest mobile phase concentration may be limited by the solubility of the additive. As described hereinabove, a suitable mobile phase concentration of any of the nitrogen-containing additives, and a corresponding column temperature for performing tcDHPLC analysis, can be readily selected by one skilled in the art, by analyzing known mixtures of heteroduplex and homoduplex molecules.

In one embodiment of tcDHPLC, all of the fragments being analyzed are eluted using the same gradient of organic solvent (e.g. acetonitrile). In other embodiments, in order to minimize the time required for analysis of multiple samples, the solvent gradient is adjusted so that all of the samples elute within a narrow range of retention time (e.g. between 5 and 6 min). As described previously (U.S. Pat. No. 6,287,822), and as observed by Applicants when using the mobile phase additives described herein, there is a highly reproducible relationship between length in base pairs vs. acetonitrile concentration (or % of buffer B). This relationship can be used to select a preferred mobile phase gradient for tcDHPLC.

In another aspect, the invention concerns kits for use in determining the presence of a mutations DNA by temperature-compression denaturing high performance liquid chromatography (tcDHPLC). A kit of the invention can include one or more of the following:

- in a separate container, a mobile phase for use in tcDHPLC, wherein the mobile phase includes at least one nitrogen containing compound as described herein. Examples of preferred nitrogen-containing additives include betaine, tetramethylammonium chloride, tetraethylammonium chloride, triethylamine hydrochloride, and choline. A preferred mobile phase includes an organic solvent and an ion pairing agent, and can include a chelating agent such as EDTA; an aqueous mobile phase including 4M betaine, 100 mM TEAA in 5% acetonitrile; an aqueous mobile phase including of 4M betaine, 100 mM TEAA in 15% acetonitrile.
- a reverse phase column containing separation beads for separating double stranded DNA by temperature-compression denaturing high performance liquid chromatography, wherein said beads comprise polymeric beads or silica particles;
- a chromatography system for performing denaturing high performance liquid chromatography;
- one or more DNA polymerases, each in a separate container. The DNA polymerase is preferably a proof reading polymerase. Non-limiting examples of a suitable proof reading polymerase include Taq, Tbr, Tfl, Tru, Tth, Tli, Tac, Tne, Tma, Tih, Tfi, Pfu, Pwo, Kod, Bst, Sac, Sso, Poc, Pab, Mth, Pho, ES4, VENT™, DEEPVENT™, PFUTurbo™, AmpliTaq®, AccuType™ and active mutants, variants and derivatives thereof. Preferred polymerase for use in the kit includes at least one of Pho (Optimase polymerase), Taq, Pfu or mixtures thereof;
- in a separate container, a mutation standard for conducting tcDHPLC. Examples of preferred mutation standards include DYS271, HTM219, and GCH338;
- in separate containers, pre-selected primers for amplifying a target DNA suspected of having a mutation therein, the amplicon being 100 to 1000 base pairs, and preferably between 200 and 500 base pairs in length;
- instructional material.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All patent applications, patents, and literature references cited in this specification are hereby incorporated by reference in their entirety. In case of conflict or inconsistency, the present description, including definitions, will control. Unless mentioned otherwise, the techniques employed or contemplated herein are standard methodologies well known to one of ordinary skill in the art. The materials, methods and examples are illustrative only and not limiting.

All numerical ranges in this specification are intended to be inclusive of their upper and lower limits.

Other features of the invention will become apparent in the course of the following descriptions of exemplary embodiments which are given for illustration of the invention and are not intended to be limiting thereof.

Procedures described in the past tense in the Examples below have been carried out in the laboratory. Procedures described in the present tense have not yet been carried out in the laboratory, and are constructively reduced to practice with the filing of this application.

EXAMPLE 1

Description of Temperature Dependent DMIPC Separation Process

This Example refers to FIG. 2 (heteroduplex separations over a 51° to 61° C. temperature range).

A DYS271 Mutation Standard (part no. 700210, Transgenomic) was hybridized and injected onto a reverse phase separation column (50 mm×4.6 mm ID) (DNASep® column, Transgenomic) at 51° C. The column was eluted at 0.9 ml/min with a gradient of acetonitrile in 0.1 M TEAA over 7 minutes. The chromatography was monitored at 260 nm using an UV detector.

The heteroduplex present in the mixture was not denatured at 51° C.; therefore, a single peak was observed (FIG. 2). The injection and chromatography of the sample was repeated at 1° C. incremental increases in temperature. A shoulder was observed on the low retention time side of the main peak at 53° C. indicating the potential presence of a heteroduplex. At 54° C. three peaks were seen. And at 55°–58° C. four peaks were seen indicating the definite presence of a mutation. The two lower retention time peaks were two heteroduplexes and the higher retention time peaks were homoduplexes.

EXAMPLE 2

DHPLC Analysis of DNA Samples using Mobile Phase Lacking Betaine

DHPLC analyses were performed using a Transgenomic Model 3500HT WAVE® nucleic acid fragment analysis system. The system consisted of an Hitachi D-7000 interface, Hitachi D-7100 pump, Hitachi D-7250 autosampler, Hitachi D-7300 column heater with stainless preheat, Hitachi D-7400 UV detector, set at 260 nm, ERC-345a vacuum degasser module, and an Intel Pentium computer including Hitachi HSM control and acquisition software and WAVE-MAKER® v. 4.1.38 software (Transgenomic). The aqueous mobile phase consisted of Buffer A: 100 mM triethylammonium acetate (TEM) (Transgenomic), and Buffer B: 100 mM TEAA in 25% acetonitrile (VWR Scientific). High purity water used for preparing buffer solutions was obtained using a Milli-Q water system (Millipore, Milford, Mass.). The buffers can be made to an all gravimetric formulation i.e. all components can be weighed out), and can be prepared under temperature controlled conditions (e.g. in a water bath).

Three mutation standards were analyzed under the conditions shown in Table 1.

TABLE 1

| FIG. | Sample | Trans-genomic part no. | Injection vol. (μl) | Betaine in mobile phase (M) | Column temp (° C.) | Flow rate (ml/min) |
|---|---|---|---|---|---|---|
| 3 | DYS271 | 700210 | 8 | 0 | 56.0 | 0.9 |
| 4 | HTM219 | 700220 | 4 | 0 | 70.0 | 0.9 |
| 5 | GCH338 | 700215 | 6 | 0 | 63.0 | 0.9 |

Figure 3:
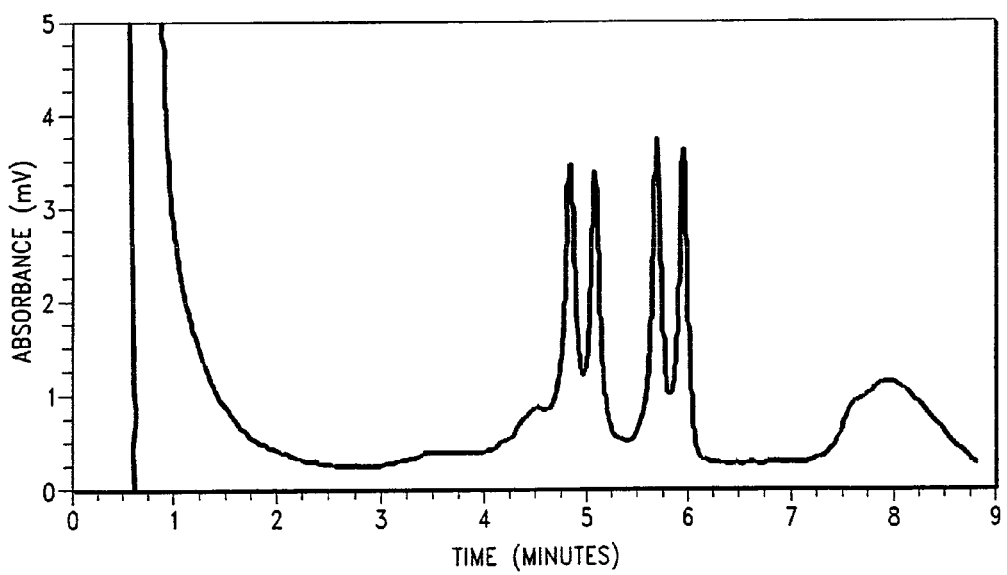
FIG. 3 is a mutation separation profile of a first mixture of homoduplex and heteroduplex molecules.
Figure 4:
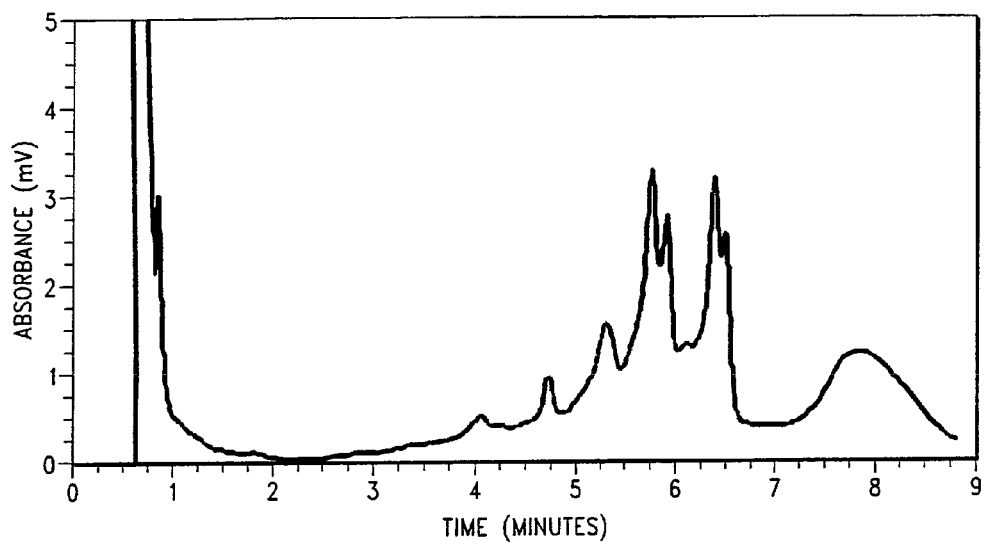
FIG. 4 is a mutation separation profile of a second mixture of homoduplex and heteroduplex molecules.
Figure 5:
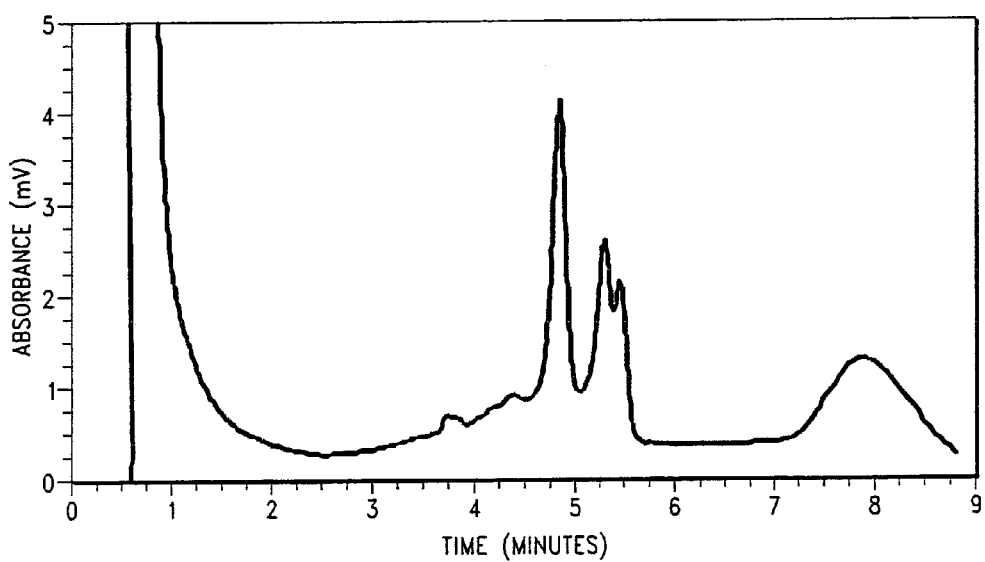
FIG. 5 is a mutation separation profile of a third mixture of homoduplex and heteroduplex molecules.

In FIGS. 3–5, the separation column (6.5 mm ID×37 mm) contained alkylated poly(styrene-divinylbenzene) beads (DNASep®) HT, Transgenomic). The column was eluted at a flow rate of 0.9 ml/min, with the gradient shown in Table 2.

TABLE 2

| Time | % B |
|---|---|
| 0.0 | 50 |
| 0.5 | 55 |
| 5.0 | 64 |
| 5.1 | 100 |
| 5.6 | 100 |
| 5.7 | 50 |
| 6.6 | 50 |

The DYS271 Mutation Standard contained equal amounts of the double stranded sequence variants 168A and 168G of the 209 base pair fragment from the human Y chromosome locus DYS271 (GenBank accession Number S76940). The A→G transition position 168 in the sequence was reported by Seielstad et al. (Human Molecular Genetics 3:2159–2161 (1994)) and the preparation of the variants has been described (Narayanaswami et al, Genetic Testing 5:9–16 (2001)). The following is the sequence of the 168A variant:

AGGCACTGGTCAGAATGAAGTGAATGGCACACAGGACAAGTCCAGACCCAGGAAGGTCC (SEQ ID NO:1)

AGTAACATGGGAGAAGAACGGAAGGAGTTCTAAAATTCAGGGCTCCCTTGGGCTCCCCT

GTTTAAAAATGTAGGTTTTATTATTATATTTCATTGTTAACAAAAGTCCATGAGATCTG

TGGAGGATAAAGGGGGAGCTGTATTTTCCATT

The variants are present at a DNA concentration of 45 μg/mL and suspended in 10 mM Tris-HCl, pH 8, 1 mM EDTA. This Mutation Standard is available commercially from Transgenomic and a similar standard is available from Varian (Walnut Creek, Calif.).

The HTM219 Mutation Standard contained equal amounts of the double stranded sequence variants 46C and 46G in a 219 base pair fragment. The following is the sequence of the 46C variant:

TTCCCTGGGTGGCCGCCGAGACGCTGGCCCGGGCTGGAGGGATGGCGGGCGGGACGG (SEQ ID NO:2)

GGGCGGGGCGGGGCTCGTCACGTGGAGAGGCGCGCGGGGCGGGCGGGGCGGGGCGC

GCGCCCGGCTCCTTAAAGGCGCGCGAGCCGAGCGGCGAGGTGCCTCTGTGGCCGCAGGC

GCAGGCCCGGGCGACAGCCGAGACGTGGAGCGCGCCGGCTCG

The GCH338 Mutation Standard contained equal amounts of the double stranded sequence variants 195C and 195T in a 338 base pair fragment. The following is the sequence of the 195T variant:

TAATACGACTCACTATAGGGCGAATTGGGCCCGACGTCGCATGCTCCCGGCCGCCATGG (SEQ ID NO:3)

CCGCGGGATTTCACTTCTAGTGCACCATTATGACGTTACTAAAGGCAGATGCAGACTTA

-continued

```
CGTTGCTTCAACCACTACCCCGACTCCAGCAGGCCGCAAGGCTTCCGTGATTGCTACAG

CAATTTGTTTTGTAAGGTGCTCCTGAACTGTGGATGTGATAAGGAGCTCAGTTTGAGAG

TCTGACACAATCACTAGTGCGGCCGCCTGCAGGTCGACCATATGGGAGAGCTCCCAACG

CGTTGGATGCATAGCTTGAGTATTCTATAGTGTCACCTAAATA
```

Prior to DHPLC analysis, each sample was subjected to the following hybridization procedure: denaturation at 95° C. for 12 minutes, followed by slow cooling to 25° C. over a 30 min period.

As seen in FIGS. 3–5, a different column temperature is required in order to observe the heteroduplexes for each mutation standard.

EXAMPLE 3 tcDHPLC Analysis of DNA Samples using Mobile Phase Containing Betaine

The tcDHPLC analyses performed in this Example used a Transgenomic Model 3500 HT WAVE system as described in Example 2. The Mutation Standards described in Example 2 were subjected to DHPLC analysis in which the mobile phase contained betaine. The mobile phase included: Buffer A consisting of 4M betaine (ICN), 100 mM TEAA in 5% acetonitrile; and Buffer B consisting of 4M betaine, 100 mM TEAA in 15% acetonitrile. Betaine was prepared as a stock 5M solution and filtered through CHELEX®-100 (catalog no. 142–2832, BioRad Laboratories, Richmond, Calif.) prior to use in the preparation of the mobile phase buffers.

Figure 6:
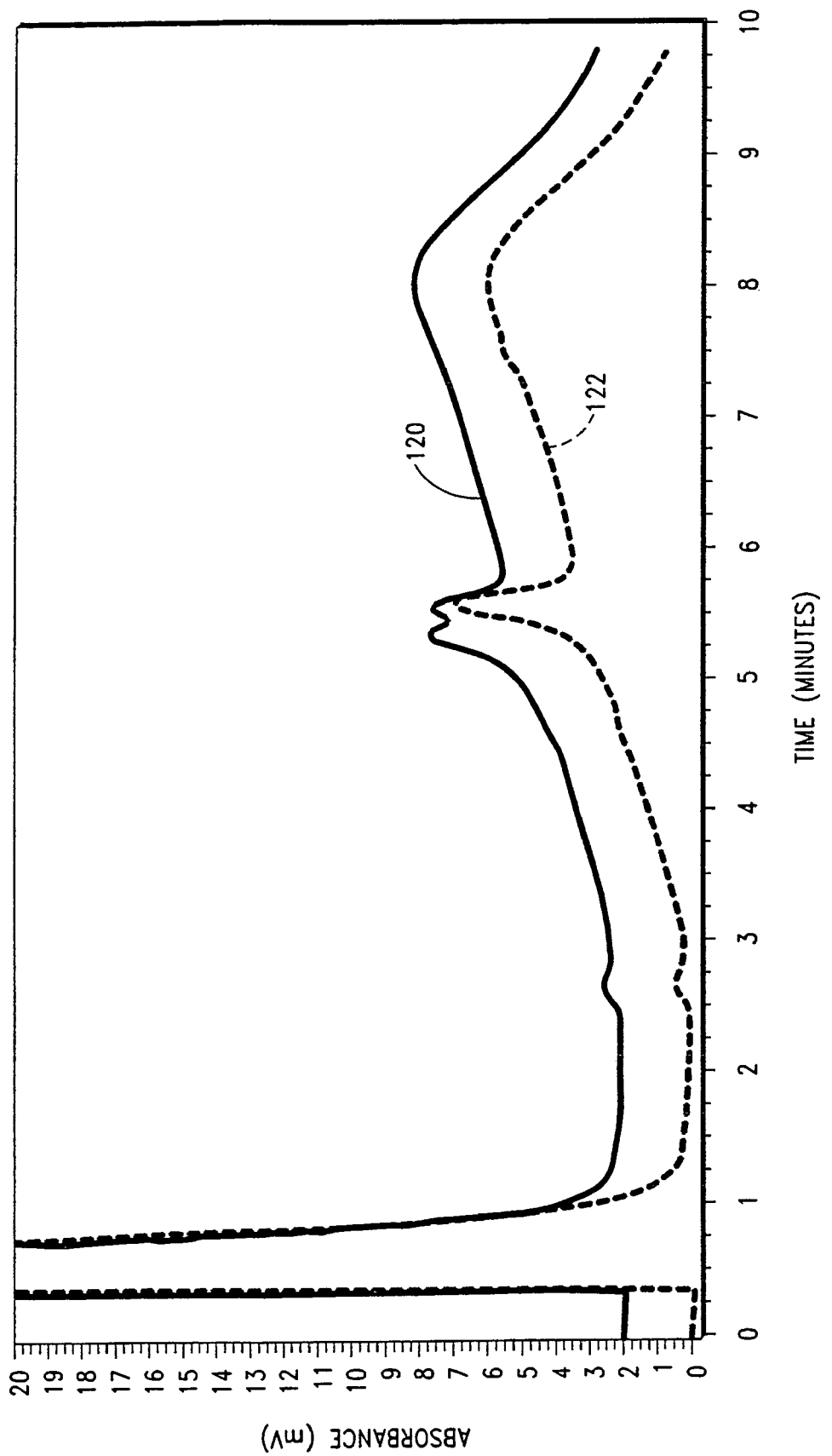
FIG. 6 is a mutation separation profile of the first mixture of molecules from FIG. 3 in which the elution was performed with a mobile phase containing an exemplary nitrogen-containing additive.
Figure 7:
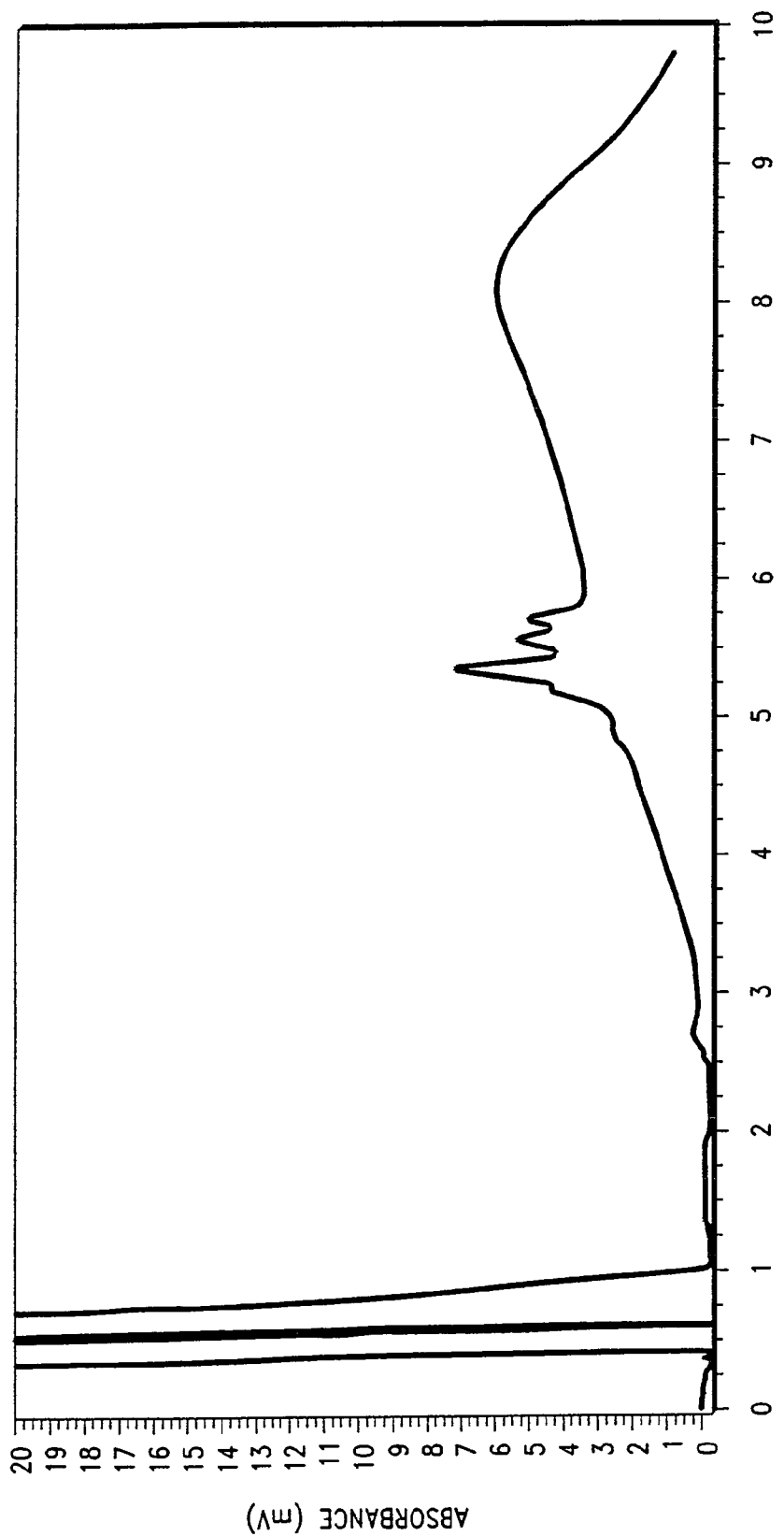
FIG. 7 is a mutation separation profile of the second mixture of molecules from FIG. 4 in which the elution was performed with a mobile phase containing the exemplary nitrogen-containing additive of FIG. 6.

In FIGS. 6 and 7, the column (4.0 mm ID×10 mm) contained alkylated poly(styrene-divinylbenzene) beads (Transgenomic). For the DYS271 and the HTM219 samples, the column was eluted at a flow rate of 0.3 ml/min, with the gradient of Table 3.

TABLE 3

| Time | % B |
|---|---|
| 0.0 | 45 |
| 0.5 | 55 |
| 4.5 | 90 |
| 4.6 | 100 |
| 5.6 | 100 |
| 5.7 | 45 |
| 6.6 | 45 |

Figure 8:
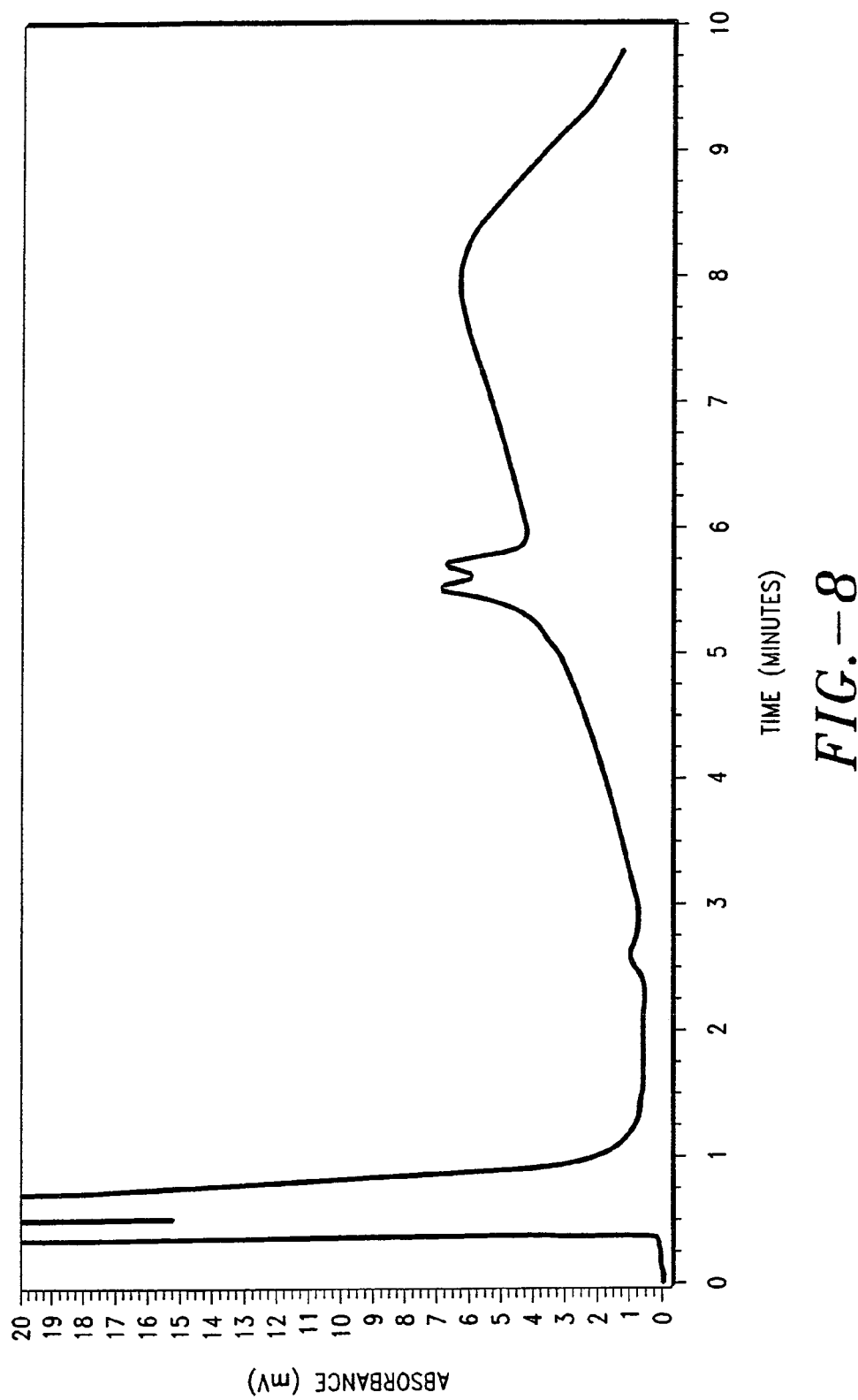
FIG. 8 is an elution profile of the third mixture of molecules from FIG. 5 in which the elution was performed with a mobile phase containing the exemplary nitrogen-containing additive of FIG. 7.

In FIG. 8, for the GCH338 sample, the column was eluted at a flow rate of 0.3 ml/min, with the gradient of Table 4.

TABLE 4

| Time | % B |
|---|---|
| 0.0 | 55 |
| 0.5 | 65 |
| 4.5 | 100 |
| 4.6 | 100 |
| 5.6 | 100 |
| 5.7 | 45 |
| 6.8 | 45 |

The three mutation standards were analyzed under the conditions shown in Table 5.

TABLE 5

| FIG. | Sample | Injection vol. (μl) | Betaine in mobile phase (M) | Column temp (° C.) | Flow rate (ml/min) |
|---|---|---|---|---|---|
| 6 | DYS271 | 2 | 4 | 43.0 | 0.3 |
| 7 | HTM219 | 1 | 4 | 43.0 | 0.3 |
| 8 | GCH338 | 2 | 4 | 43.0 | 0.3 |

In FIG. 6, profile 120 represents the elution chromatogram of the DYS271 Mutation Standard after hybridization, showing multiple peaks due to the formation of heteroduplexes. For comparison, profile 122 shows the chromatogram of the DYS271 Mutation Standard prior to hybridization, showing a single peak due to the homoduplex molecules in the mixture. The hybridization is schematically illustrated in scheme 100 of FIG. 1.

In contrast to Example 2, Example 3 (FIGS. 6–8) illustrates conditions which allowed observation (i.e. detection) of heteroduplexes from all of the three Mutation Standards when the analysis was carried out at the same temperature (i.e. 43° C.).

Figure 9:
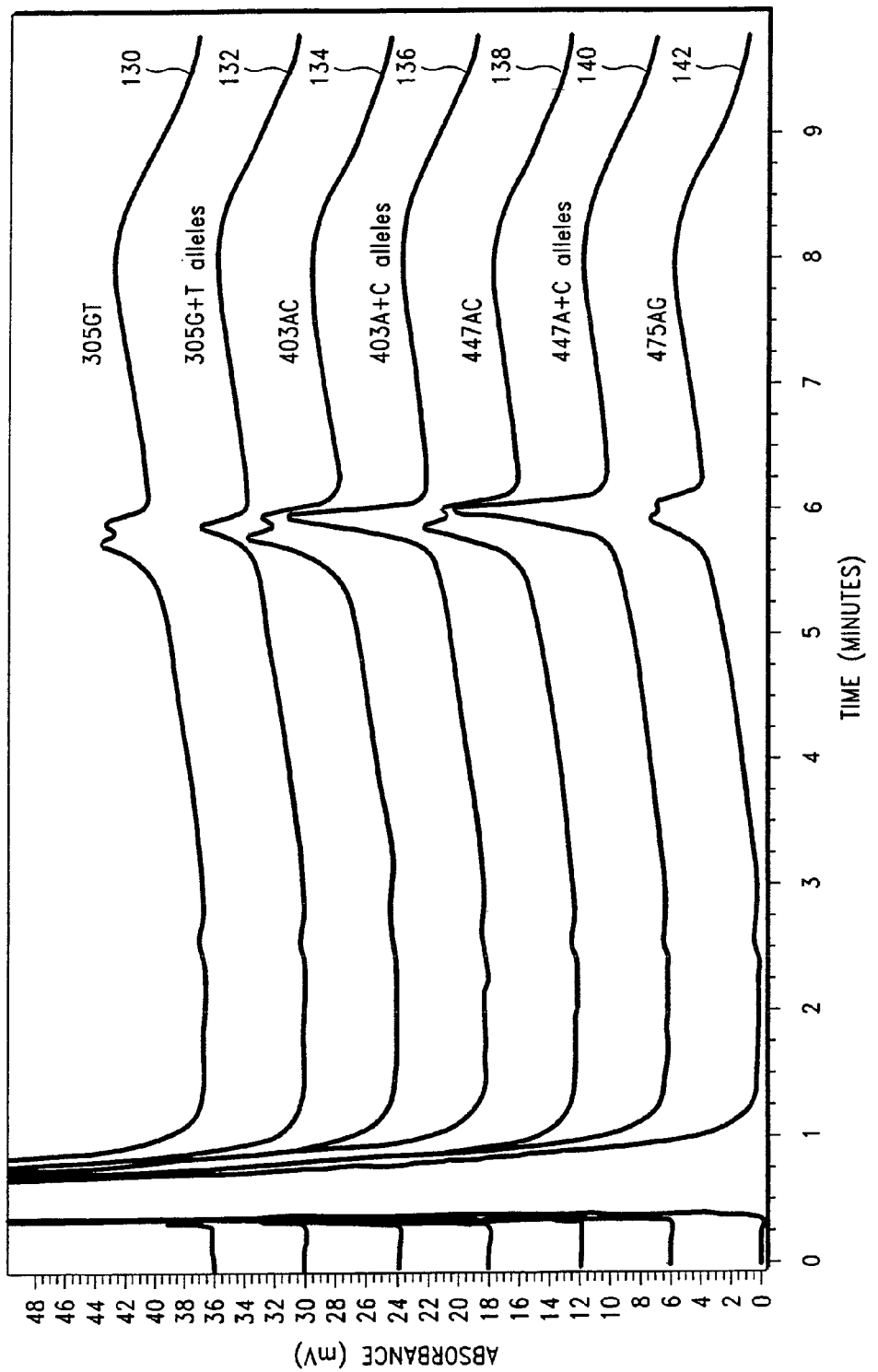
FIG. 9 illustrates analysis of four different mixtures of homoduplex and heteroduplex molecules by temperature-compression DHPLC.

EXAMPLE 4 tcDHPLC Analysis of a Plurality of Different Heteroduplex Molecules at a Single-Temperature FIG. 9 shows the elution profiles of four mixtures of double stranded DNA molecules. Each mixture was analyzed under the same conditions as the mixture in FIG. 8. The profiles are identified as shown in Table 6.

TABLE 6

| Chromatograph no. | Name | Fragment length (bp) | Hybridized |
|---|---|---|---|
| 130 | 305GT | 305 | yes |
| 132 | 305G + T | 305 | no |
| 134 | 403AC | 403 | yes |
| 136 | 403A + C | 403 | no |
| 138 | 447AC | 447 | yes |
| 140 | 447A + C | 447 | no |
| 142 | 475AG | 475 | yes |

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

All patent applications, patents, and literature references cited in this specification are hereby incorporated by reference in their entirety. In case of conflict or inconsistency, the present description, including definitions, will control.

The invention claimed is:

1. A chromatographic method for separating heteroduplex and homoduplex DNA molecules in a test mixture, said method comprising:
   (a) applying the test mixture to a reverse phase separation medium;
   (b) eluting the medium of step (a) with a mobile phase comprising betaine, wherein said eluting is carried out at 20° C. to 80° C. and wherein the eluting results in the separation of said heteroduplexes from said homoduplexes;
   wherein said eluting is carried out at a pre-selected concentration of betaine and at a pre-selected temperature;
   wherein said betaine is present at a concentration at which first heteroduplex molecules from a first mixture can be observed at said pre-selected temperature, and wherein second heteroduplex molecules from a second mixture can be observed at said pre-selected temperature;
   wherein said first mixture comprises a hybridization product of the double stranded sequence variant 168A and sequence variant 168G, wherein the 168A variant corresponds to the nucleic acid identified by SEQ ID NO:1; and,
   wherein said second mixture comprises a hybridization product of the double stranded sequence variant 46C and sequence variant 46G, wherein the 46C variant corresponds to the nucleic acid identified by SEQ ID NO:2.

2. The method of claim 1, wherein said mobile phase comprises: an organic solvent and a counterion agent.

3. The method of claim 1 wherein said mobile phase possess a pH in the range of 4 to 9.

4. The method of claim 1 wherein betaine is present at a concentration in the range of about 0.5 to about 6 M.

5. The method of claim 1 wherein betaine is present at a concentration in the range of about 2 to about 5 M.

6. The method of claim 1 wherein said mobile phase comprises an aqueous mobile phase.

7. The method of claim 1 wherein said betaine has been treated with activated charcoal.

8. The method of claim 1 wherein said betaine has been treated with an ion-exchange resin.

9. The method of claim 8 wherein said resin comprises chelex-100.

10. The method of claim 2 wherein said counterion agent comprises triethylammonium acetate.

11. The method of claim 1 wherein said betaine is present at a concentration of 4M and said temperature is 43° C.

12. The method of claim 1 wherein the eluting is carried out at a temperature in the range of about 25+ C. to about 80° C.

13. The method of claim 1 wherein the eluting is carried out at a temperature in the range of about 30° C. to about 50° C.

14. The method of claim 1 wherein the eluting is carried out at a temperature less than about 50° C.

15. A chromatographic method for separating heteroduplex and homoduplex DNA molecules in a mixture, said method comprising:
(a) applying the mixture to a reverse phase separation medium;
(b) eluting the medium of step (a) with a mobile phase comprising a nitrogen-containing additive, wherein said eluting is carried out at 20° C. to 80° C. and wherein the eluting results in the separation of said heteroduplexes from said homoduplexes,
wherein said eluting is carried out at a pre-selected concentration of said nitrogen-containing additive and a at pre-selected temperature;
wherein said additive is present at a concentration at which first heteroduplex molecules from a first mixture can be observed at said pre-selected temperature, and wherein second heteroduplex molecules from a second mixture can be observed at said pre-selected temperature;
wherein said first mixture comprises a hybridization product of the double stranded sequence variant 168A and sequence variant 168G of a first fragment, wherein the 168A variant corresponds to the nucleic acid identified by SEQ ID NO:1; and,
wherein said second mixture comprises a hybridization product of the double stranded sequence variant 46C and sequence variant 46G of a second fragment, wherein the 46C variant corresponds to the nucleic acid identified by SEQ ID NO:2;
wherein said nitrogen-containing additive comprises a compound according to the formula:

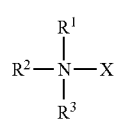

(I)

wherein: $R^1$, $R^2$, and $R^3$, may be the same or different and are independently selected from the group consisting of hydrogen, methyl, ethyl, hydroxyethyl, and propyl, with the proviso that no more than two of $R^1$, $R^2$, and $R^3$ are hydrogen; and X is a moiety selected from the group consisting of: radicals of the formulas

=O;

→O;

—$CH_3$;

—$CH_2CH_3$; and

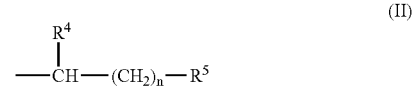

(II)

wherein:
$R^4$ is selected from the group consisting of methyl and hydrogen and, when combined with $R^1$, forms a pyrrolidine ring;
$R^5$ is selected from the group consisting of —$CO_2H$, —$CH_2OH$, and —$SO_3H$; and
n is an integer of from 0 to 2;
with the proviso that, when $R^1$ and $R^4$ form a pyrrolidine ring, no more than one of $R^2$ and $R^3$ is hydrogen.

16. The method of claim 15 wherein $R^1$, $R^2$ and $R^3$ are the same or different and selected from the group consisting of methyl, ethyl and hydrogen with the proviso that no more than two of $R^1$, $R^2$ and $R^3$ are hydrogen and, when $R^1$ and $R^4$ form a pyrrolidine ring, no more than one of $R^2$ and $R^3$ is hydrogen.

17. The method of claim 16 wherein X is —$CH_2CO_2H$.

18. The method of claim 16 wherein X is —$CH_2CO_2H$ and wherein $R^1$, $R^2$, and $R^3$ are methyl.

19. The method of claim 17 wherein $R^1$, $R^2$ and $R^3$ are methyl.

20. The method of claim 17 wherein $R^1$ and $R^2$ are methyl and $R^3$ is hydrogen.

21. The method of claim 17 wherein $R^1$ is methyl and $R^2$ and $R^3$ are hydrogen.

22. The method of claim 16 wherein X is =O.

23. The method of claim 22 wherein $R^1$, $R^2$ and $R^3$ are methyl.

24. The method of claim 16 wherein $R^1$ and $R^4$ form a pyrrolidine ring, $R^2$ and $R^3$ methyl, n is 0, and $R^5$ is —$CO_2H$.

25. The method of claim 16 wherein $R^1$, $R^2$ and $R^3$ are methyl and X is —$CH_2SO_3$.

26. The method of claim 15 wherein the composition comprises trimethylglycine.

27. A kit for use in temperature-compression denaturing high performance liquid chromatography, said kit comprising, in separate containers:
(a) double-stranded DNA comprising the nucleic acid sequence of SEQ ID NO:1,
(b) double-stranded DNA comprising the nucleic acid sequence of SEQ ID NO:2, and
(c) Pho DNA polymerase.

28. The kit of claim 27 further including, in a separate container, mobile phase comprising betaine.

29. The kit of claim 27 further including, in a separate container, mobile phase comprising a nitrogen-containing additive, wherein said nitrogen-containing additive comprises a compound according to the formula:

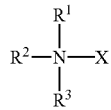 (I)

wherein:
$R^1$, $R^2$, and $R^3$, may be the same or different and are independently selected from the group consisting of hydrogen, methyl, ethyl, hydroxyethyl, and propyl, with the proviso that no more than two of $R^1$, $R^2$, and $R^3$ are hydrogen; and X is a moiety selected from the group consisting of:
radicals of the formulas

=O;

→O;

—CH$_3$;

—CH$_2$CH$_3$; and

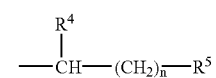 (II)

wherein:
$R^4$ is selected from the group consisting of methyl and hydrogen and, when combined with $R^1$, forms a pyrodine ring;
$R^5$ is selected from the group consisting of —CO$_2$H, —CH$_2$OH, and —SO$_3$H; and
n is an integer of from 0 to 2;
with the proviso that, when $R^1$ and $R^4$ form a pyrrolidine ring, no more than one of $R^2$ and $R^3$ is hydrogen.

* * * * *